United States Patent
Fleishman et al.

(10) Patent No.: US 12,331,324 B2
(45) Date of Patent: Jun. 17, 2025

(54) VERSATILE PEROXIDASES AND USES THEREOF

(71) Applicant: Yeda Research and Development Co. Ltd., Rehovot (IL)

(72) Inventors: Sarel Fleishman, Rehovot (IL); Shiran Barber-Zucker, Rehovot (IL)

(73) Assignee: Yeda Research and Development Co. Ltd., Rehovot (IL)

(*) Notice: Subject to any disclaimer, the term of this patent is extended or adjusted under 35 U.S.C. 154(b) by 0 days.

(21) Appl. No.: 18/672,113

(22) Filed: May 23, 2024

(65) Prior Publication Data

US 2024/0301368 A1    Sep. 12, 2024

Related U.S. Application Data

(63) Continuation of application No. PCT/IL2022/051256, filed on Nov. 24, 2022.

(60) Provisional application No. 63/282,678, filed on Nov. 23, 2021.

(51) Int. Cl.
| | |
|---|---|
| C12N 15/18 | (2006.01) |
| C12N 9/08 | (2006.01) |
| C12N 15/81 | (2006.01) |
| C12P 7/10 | (2006.01) |

(52) U.S. Cl.
CPC ............ *C12N 9/0065* (2013.01); *C12N 15/81* (2013.01); *C12P 7/10* (2013.01); *C12Y 111/01007* (2013.01)

(58) Field of Classification Search
CPC .................. C12Y 111/01013; C12Y 111/01007
USPC ...................................................... 435/189
See application file for complete search history.

(56) References Cited

FOREIGN PATENT DOCUMENTS

| CN | 107815459 | 3/2018 |
|---|---|---|
| WO | WO 2012/068167 | 5/2012 |
| WO | WO 2023/095139 | 6/2023 |

OTHER PUBLICATIONS

International Search Report and the Written Opinion Dated Feb. 15, 2023 From the International Searching Authority Re. Application No. PCT/IL2022/051256. (22 Pages).
Barber-Zucker et al. "Stable and Functionally Diverse Versatile Peroxidases Designed Directly From Sequences", Journal of the American Chemical Society, JACS, XP093021453, 144(8): 3564-3571, Published Online Feb. 18, 2022.
Bernini et al. "Prediction of Hydrogen-Bonding Networks Around Tyrosyl Radical in P. Eryngii Versatile Peroxidase W164Y Variants: A QM/MM MD Study", Molecular Simulation, XP093021456, 40(6): 485-490, Aug. 6, 2013.
Bronikowski et al. "Redesign of a New Manganese Peroxidase Highly Expressed in Pichia Pastoris Towards a Lignin-Degrading Versatile Peroxidase", ChemBioChem, XP093021451, 19(23): 2481-2489, Published Online Nov. 20, 2018.
Garcia-Ruiz et al. "Directed Evolution of a Temperature-, Peroxide- and Alkaline PH-Tolerant Versatile Peroxidase", Biochemical Journal, XP093021521, 441(1): 489-498, Jan. 1, 2012.
Gonzalez-Perez et al. "Structural Determinants of Oxidative Stabilization in an Evolved Versatile Peroxidase", ACS Catalysis, XP093021529, 4(11): 3891-3901, Sep. 22, 2014.
Perez-Boada et al. "Versatile Peroxidase Oxidation of High Redox Potential Aromatic Compounds: Site-Directed Mutagenesis, Spectroscopic and Crystallographic Investigation of Three Long-Range Electron Transfer Pathways", Journal of Molecular Biology, XP005153231, 354(2): 385-402, Published Online Oct. 3, 2005.
Sanchez-Alejandro et al. "Tryptophan-Surface Modification of Versatile Peroxidase From Bjerkandera Adusta Enhances Its Catalytic Performance", Journal of Molecular Catalysis B: Enzymatic, XP029400808, 124: 45-51, Available Online Dec. 3, 2015.

*Primary Examiner* — Robert B Mondesi
*Assistant Examiner* — Mohammad Y Meah

(57) ABSTRACT

Recombinant peroxidase enzymes are disclosed having mutations that increase yield when expressed in yeast cells as compared to their corresponding wild-type peroxidase enzyme. Methods of generating are also disclosed as well as uses thereof.

Figures 1C, 1D:
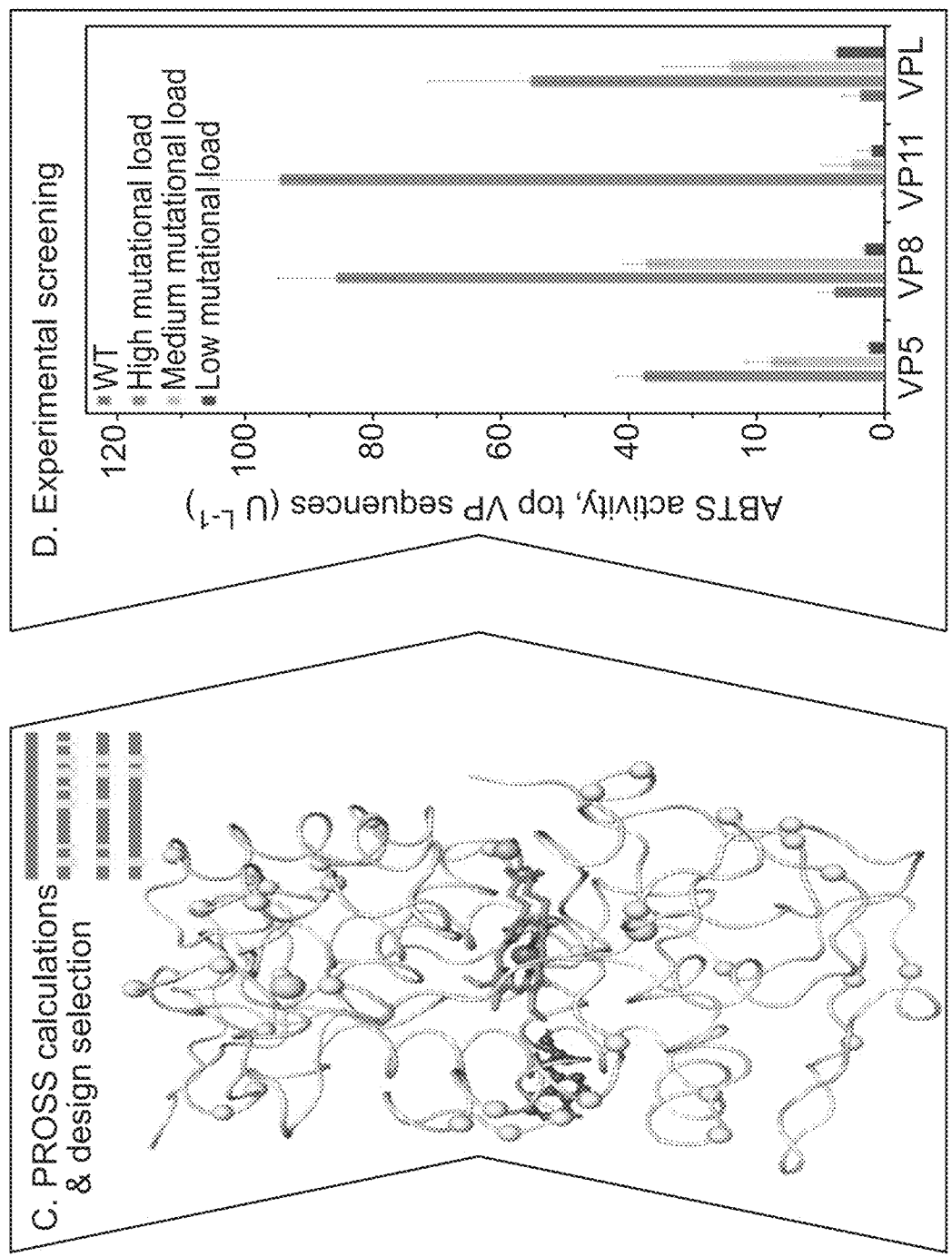

18 Claims, 16 Drawing Sheets
(16 of 16 Drawing Sheet(s) Filed in Color)
Specification includes a Sequence Listing.

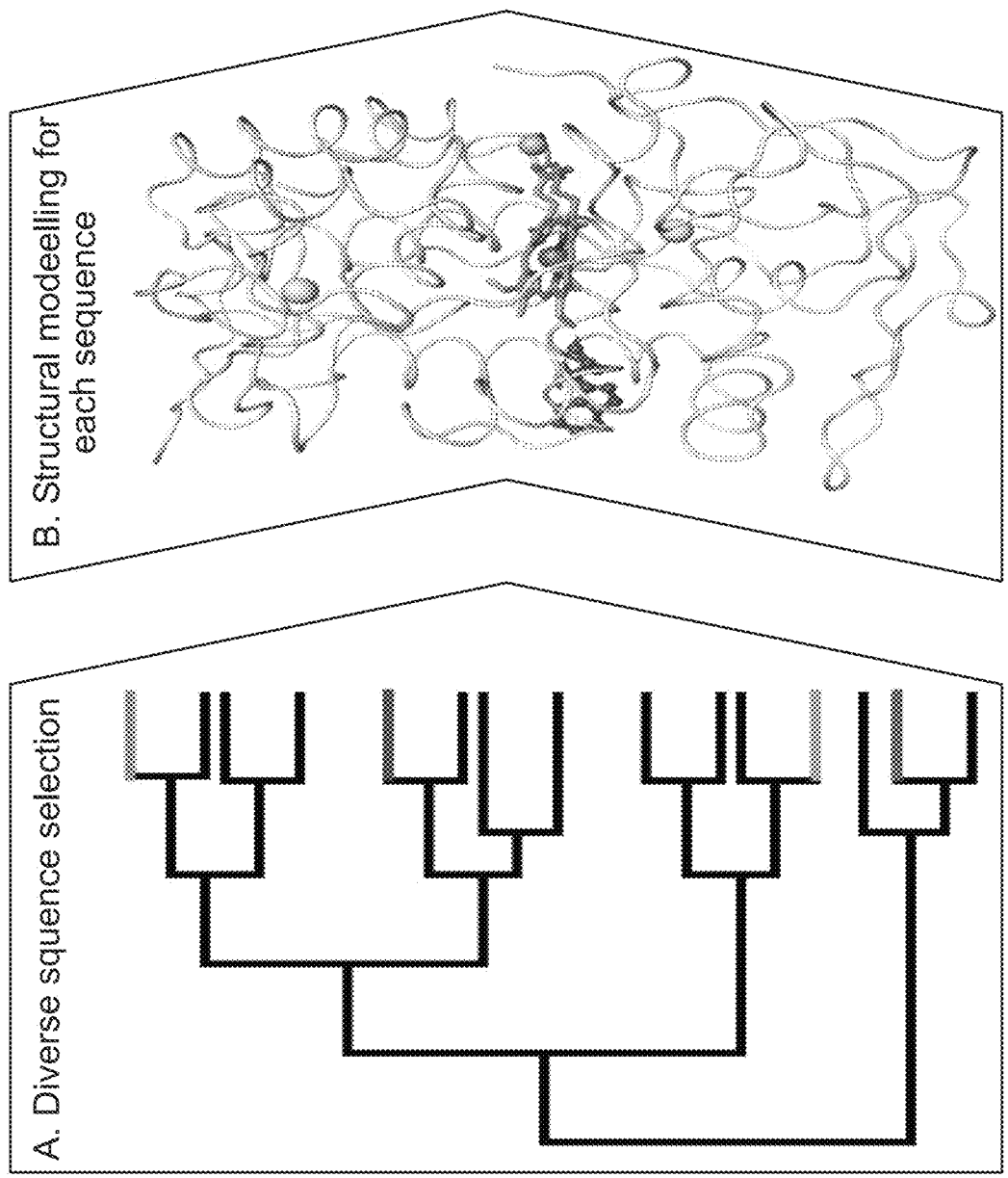

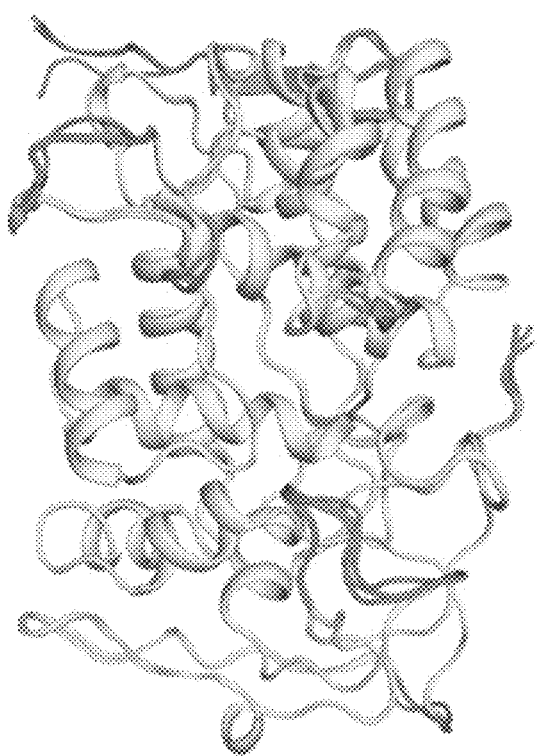 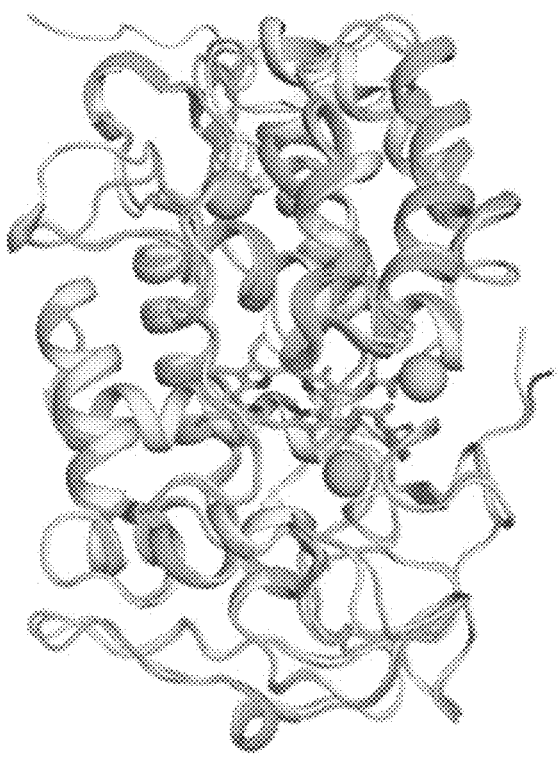
FIG. 5A  FIG. 5B
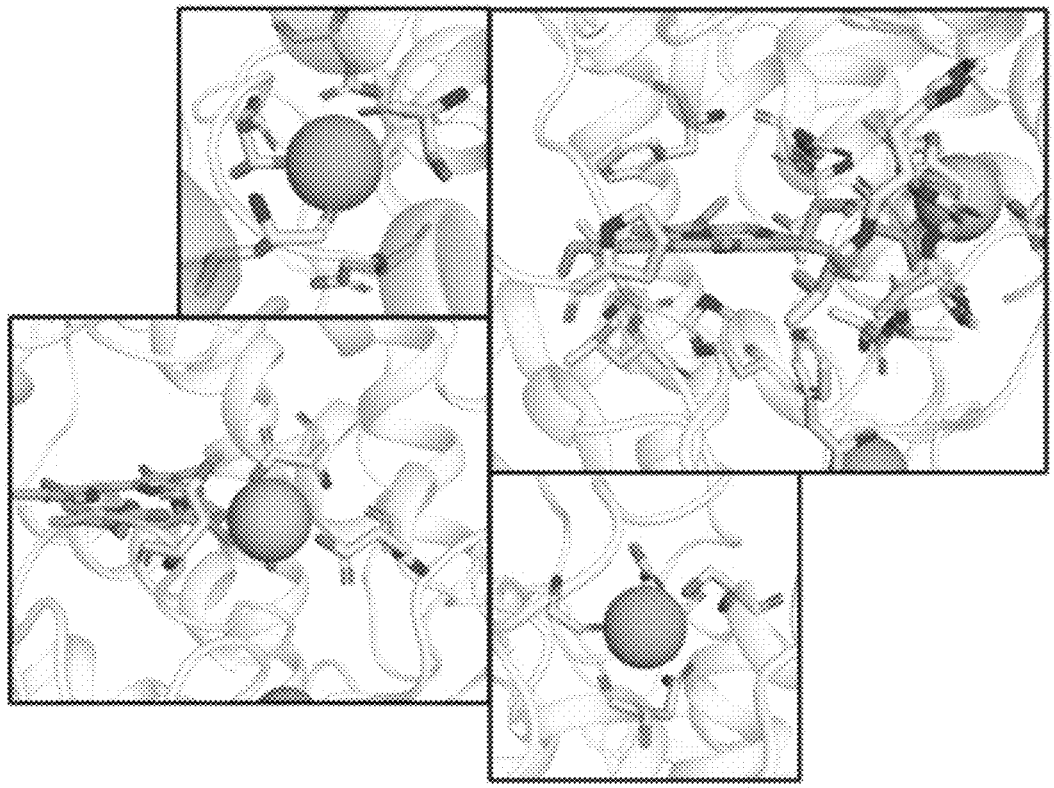
FIG. 5C

FIG. 9A

```
5WT  VSLPQKRATCAGGQVTANAACCVLFPLMEDLQKNLFDDGACGEDAHEALRLTFHDAIGFS  60
5H   VSLPQKRATCSGGQTTSNEACCVLFDLMEDLQKNLFDGGQCGEQAHEALRLTFHDAIGFS  60

5WT  PSRGVMGGADGSVITFSDTEVNFPANLGIDEIVEAEKPFLARHNISAGDLVHFAGTLAVT  120
5H   PSRGVMGGADGSVITFSDIETNFPANLGIDDIVEAEKSFLQRHNISAGDLVHFAATLAVT  120

5WT  NCPGAPRIPFFLGRPPAKAASPIGLVPEPFDTITDILARMDDAGFVSVEVWLLSAHSVA   180
5H   NCPGAPRIPFFLGRPPATAPSPPGLVPEPFDSVTDILARMADAGFSPVEVWLLSAHSVA   180

5WT  AADIVDETIPGTPFDSTPNLFDSQIFIETQLRGISFPGTGGNHGEVQSPLKGEMRLQSDH  240
5H   AADHVDPTIPGTPFDSTPNLFDSQFFIETQLRGTTFPGTGGNPGEVKSPLPGEMRLQSDH  240

5WT  LFARDDRTSCEWQSMTNDQQKIQDRFSDTLFKMSMLGQNQDAMIDCSDVIPVPAALVTKP  300
5H   LFARDPRTACEWQSMVNDQQKIQDRFRDTLFKMSMLGQNQDDMIDCSDVIPVPPPLTTKP  300

5WT  HLPAGKSKTDVEQACATGAFPALGADPGPVTSVPRVPPA                      339
5H   HLPAGKSKTDVEQACATAPFTLPADPGPPTSVPPVPPA                       339
```

FIG. 9B

| | | |
|---|---|---|
| 8WT | AVPRMGKRATCSNGKTVNNDACCVWFDVLDDIQENLFHGGQCGEDAHEALRLTFHDAIGF | 60 |
| 8H | AVPPSGKRATCSNGKTVNNDACCVWFDVLDDIQTNLFHGGQCGEDAHEALRLTFHDAIAF | 60 |
| 8WT | SPALTAAGQFGGGGADGSIIAHSDVELTYPANNGVDEIVEASRPIAIKHNVSFGDFIQFA | 120 |
| 8H | SPALWAQGQFGGGGADGSIIAHSDIELTYPANNGIDEIVEASRHIAQKHNVSFGDFIQFA | 120 |
| 8WT | GAVGTANCNGGPQLSFFAGRSNDSQPAPPNLVPLPSDSADSILSRFSDAGFDAVEVVWLL | 180 |
| 8H | GAVGVANCNGGPQLPFFAGRPNPSQPAPPNLVPLPSDSADQILARFADAGFSAVEVVWLL | 180 |
| 8WT | VSHTVGSQHTVDPSIPGAPFDSTPSDFDAQFFVETMLNGTLVPGNGLQDGEVNSPYPGEF | 240 |
| 8H | VSHTVGSQHTVDPSIPGAPFDSTPSDFDAQFFVETMLNGTLVPGNGLQQGEVNSPYPGEF | 240 |
| 8WT | RLQSDFALSRDSRTACEWQKMIADRANMLAKFEGVMLKMSLLGFDQSALTDCSDVIPTAT | 300 |
| 8H | RLQSDFLLARDPRTACEWQKMIADQDNMQSKFAAVMLKMSLLGFDQSSLIDCSDVIPTPP | 300 |
| 8WT | GTVQDPFLPAGLTVDDLQPACSSSAFPTVSTVAGAATSIPAVPMDS | 346 |
| 8H | GTVQDPFLPAGLTVDDLQPACSDSPFPTVPGPATSIPPVPMDS | 346 |

FIG. 9C

```
11WT  VTLPQKRATCAGGQVTANAACCVLFPILEDLQQNLFDGGECGEEVHESLRLTFHDAIGFS  60
11H   VTLPQKRATCSGGQTTSNAACCVLFDLRDDLQKNLFDGGQCGEEVHESLRLTFHDAIGFS  60

11WT  PTKGGGGADGSVLTFSDPEVNFPANLGIDEIVEAQKPFLARHNISAGDLVQFAGALGVSN  120
11H   PTKGGGGADGSVLIFSDTELNFPANLGIDEIVEAQKPFLQRHNISAGDLVQFAGALGVSN  120

11WT  CPGAPRIPFFLGRPPAKAASPIGLVPEPFDTVTDILDRMGDAGFAAVEVWLLSSHTIAA   180
11H   CPGAPRIPFFLGRPPATAPSPDGLVPEPFDSVDDILARMADAGFSPVEVWLLSSHTIAA   180

11WT  ADHVDESIPGTPFDSTPSIFDSQFFIETQLRGTSFPGSGGNHGEVESPLAGEIRLQSDHL  240
11H   ADHVDPTIPGTPFDSTPSIFDSQFFIETQLRGTLFPGTGGNPGEVESPLPGEIRLQSDHL  240

11WT  LARDSRTSCEWQSMVDNMPKIQNRFAATMLKMSLLGQNQADLIDCSDVIPTPPALVGKAH  300
11H   LARDPRTACEWQSMVDNMPKIQNRFAATMLKMSLLGQNVRDLIDCSDVIPTPPLVGTAH  300

11WT  LPAGKVQSDVEQACATTPFAIAADPGPVTAVPPVPPS  338
11H   LPAGKTQSDVEQACATTPFPTIPADPGPVTSVPPVPPS  338
```

VERSATILE PEROXIDASES AND USES THEREOF

RELATED APPLICATIONS

This application is a Continuation of PCT Patent Application No. PCT/IL2022/051256 having International filing date of Nov. 24, 2022 which claims the benefit of priority benefit under 35 USC § 119(e) of U.S. Provisional Patent Application No. 63/282,678, filed on Nov. 23, 2021. The contents of the above applications are all incorporated by reference as if fully set forth herein in their entirety.

SEQUENCE LISTING STATEMENT

The XML file entitled 99839SequenceListing.xml, created on Mar. 21, 2024 comprising 11,226 bytes, submitted concurrently with the filing of this application is incorporated herein by reference.

FIELD AND BACKGROUND OF THE INVENTION

The present invention, in some embodiments thereof, relates to recombinant versatile peroxidases and uses thereof.

The need for developing economical and environmentally friendly energy sources is undeniable. Efficient conversion of biomass, particularly lignocellulose, into biofuels is a promising route for sustainable and renewable energy production. The amorphous and highly cross-linked structure of lignin, however, obstructs the accessibility of chemicals and enzymes to cellulose and impedes their conversion into biofuels and other high-value chemicals. Furthermore, lignin itself comprises potentially valuable chemicals that could be valorized. Since chemical depolymerization of lignin is still not economically viable or environmentally benign, biodegradation is an attractive route for utilization of wood biomass.

The most efficient natural system for lignin depolymerization is observed in white-rot basidiomycetes. These fungi secrete a repertoire of high-redox potential oxidoreductases (laccases and peroxidases) that degrade lignin synergistically. Of these, versatile peroxidases (VPs; EC 1.11.1.16) are of particular interest for biotechnological use due to their broad substrate scope ranging from low- to high-redox potential substrates. VPs reduce hydrogen peroxide by oxidizing a wide range of substances, including phenolic and nonphenolic compounds, pesticides, high-redox potential dyes, polycyclic aromatic hydrocarbons, and lignin. Some fungal species secrete several VP paralogs, suggesting that VPs may act synergistically. Nevertheless, VPs are especially challenging for heterologous production, limiting their use in research, let alone as an enzyme repertoire or in industrial applications.

One reason why VPs are functionally promiscuous is that they comprise three distinct active sites for substrate oxidation: a site for the oxidation of Mn2+ to Mn3+, which acts as a diffusible mediator, a low-redox potential heme-dependent binding pocket, and a high-redox potential surface-reactive tryptophan radical, which connects to the heme through a long-range electron-transfer pathway. Additionally, they comprise two structural calcium ions, multiple glycosylations, and several disulfide bonds, thereby complicating their expression in heterologous hosts. Thus, to date, only a VP from *Pleurotus eryngii* (VPL) has been fully characterized biochemically and structurally (Pérez-Boada et al., J. Mol. Biol. 2005, 354, 385-402). Several directed evolution campaigns successfully adjusted VPL to various industrial requirements: functional expression in the yeast *Saccharomyces cerevisiae*, thermostability, (Garcia-Ruiz, E et al., Biochem. J. 2012, 441, 487-498) stability and activity in neutral and alkaline pH, (Gonzalez-Perez et al., Catal. Sci. Technol. 2016, 6, 6625-6636) and stability and activity under high concentrations of $H_2O_2$, (Gonzalez-Perez et al., ACS Catal. 2014, 4, 3891-3901) which serves as the terminal electron acceptor in VPs and is also a strong inhibitor. In each such campaign, 5000-15 000 clones generated by random mutagenesis and diverse DNA recombination methods were screened to reach the desirable trait. Although successful, the high labor intensity makes directed evolution an impractical approach for optimizing multiple natural starting points. The ability of ancestral sequence reconstruction to optimize VPs is also limited as it can generate only one or few enzymes and therefore cannot expose multiple functional profiles encoded among natural homologues.

Background art includes Garcia-Ruiz, E.; Gonzalez-Perez, D. et al; Biochem. J. 2012, 441, 487-498; Gonzalez-Perez, D. et al., Catal. Sci. Technol. 2016, 6, 6625-6636; and Gonzalez-Perez, D, ACS Catal. 2014, 4, 3891-3901.

SUMMARY OF THE INVENTION

According to an aspect of some embodiments of the present invention there is provided a peroxidase enzyme comprising:
  (i) an amino acid sequence at least 85% identical to SEQ ID NO: 1; and
  (ii) mutations set forth in A11S, V15T, A17S, A19E, P26D, D38G, A40Q, D44Q, T79I, V81T, E91D, P98S, A101Q, G115A, K138T, A140P, I143P, T152S, I153V, D161A, V166S, S167P, E187P, I205F, I214T, S215T, H223P, Q227K, K231P, D246P, S249A, T256V, S267R, A282D, A294P, A295P, V297T, G318A, A319P, A322T, G324P, V330P and R335P, wherein the coordinates correspond to the SEQ ID NO: 1;
  wherein the peroxidase enzyme is characterized by increased yield when expressed in yeast cells as compared to wild-type peroxidase enzyme having an amino acid sequence as set forth in SEQ ID NO: 4.

According to some embodiments of the invention, the peroxidase is at least 95% identical to SEQ ID NO: 1.

According to some embodiments of the invention, the peroxidase is at least 99% identical to SEQ ID NO: 1.

According to an aspect of some embodiments of the present invention there is provided a peroxidase enzyme comprising:
  (i) an amino acid sequence at least 85% identical to SEQ ID NO: 2; and
  (ii) mutations set forth in R4P, M5S, E34T, G59A, T65W, A67Q, V85I, V95I, P104H, I107Q, T125V, S135P, S141P, D143P, S161Q, S164A, S167A, D172S, D229Q, A247L, S249A, S252P, R265Q, A266D, L269Q, A270S, E273A, G274A, A288S, T290I, A299P, T300P, S323D, A325P, S330P, A333P, A335P and A341P, wherein the coordinates correspond to the SEQ ID NO: 2;
  wherein the peroxidase enzyme is characterized by increased yield when expressed in yeast cells as compared to wild-type peroxidase enzyme having an amino acid sequence as set forth in SEQ ID NO: 5.

According to some embodiments of the invention, the peroxidase is at least 95% identical to SEQ ID NO: 2.

According to some embodiments of the invention, the peroxidase is at least 99% identical to SEQ ID NO: 2.

According to an aspect of some embodiments of the present invention there is provided a peroxidase enzyme comprising:
(i) an amino acid sequence at least 85% identical to SEQ ID NO: 3; and
(ii) mutations set forth in A11S, V15T, A17S, P26D, I27L, L28R, E29D, E40Q, T74I, P78T, V80L, A100Q, K137T, A139P, I142D, T151S, T153D, D157A, G160A, A165S, A166P, V306T, A321T, A323P and A331S, wherein the coordinates correspond to the SEQ ID NO: 3;
wherein the peroxidase enzyme is characterized by increased yield when expressed in yeast cells as compared to wild-type peroxidase enzyme having an amino acid sequence as set forth in SEQ ID NO: 6.

According to some embodiments of the invention, the peroxidase is at least 95% identical to SEQ ID NO: 3.

According to some embodiments of the invention, the peroxidase is at least 99% identical to SEQ ID NO: 3.

According to an aspect of some embodiments of the present invention there is provided a peroxidase enzyme comprising an amino acid sequence selected form the group consisting of SEQ ID NO: 1, SEQ ID NO: 2 and SEQ ID NO: 3.

Figure 3:
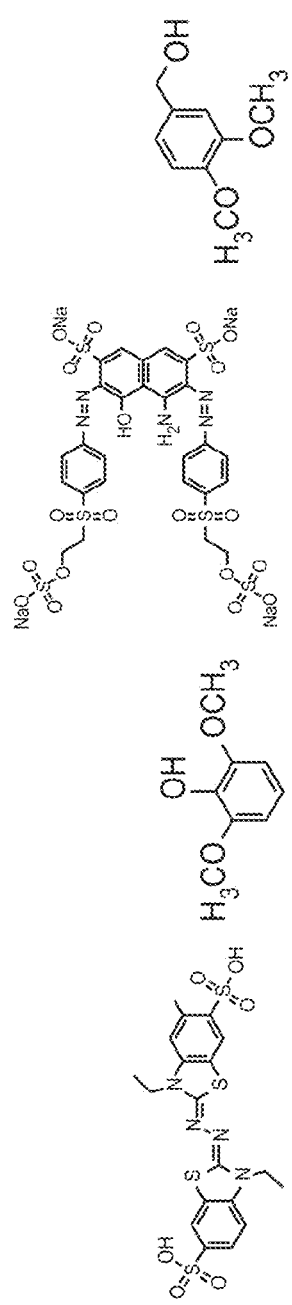

According to some embodiments of the invention, the peroxidase has a Km or a Kcat for a substrate selected from the group consisting of 2,2'-azino-bis(3-ethylbenzothiazoline-6-sulfonic acid (ABTS), 2,6-dimethoxyphenol (DMP), veratryl alcohol (VA), reactive black 5 (RB5) and $Mn^{2+}$ as set forth in Table 4 or FIG. 3.

Figure 7A:
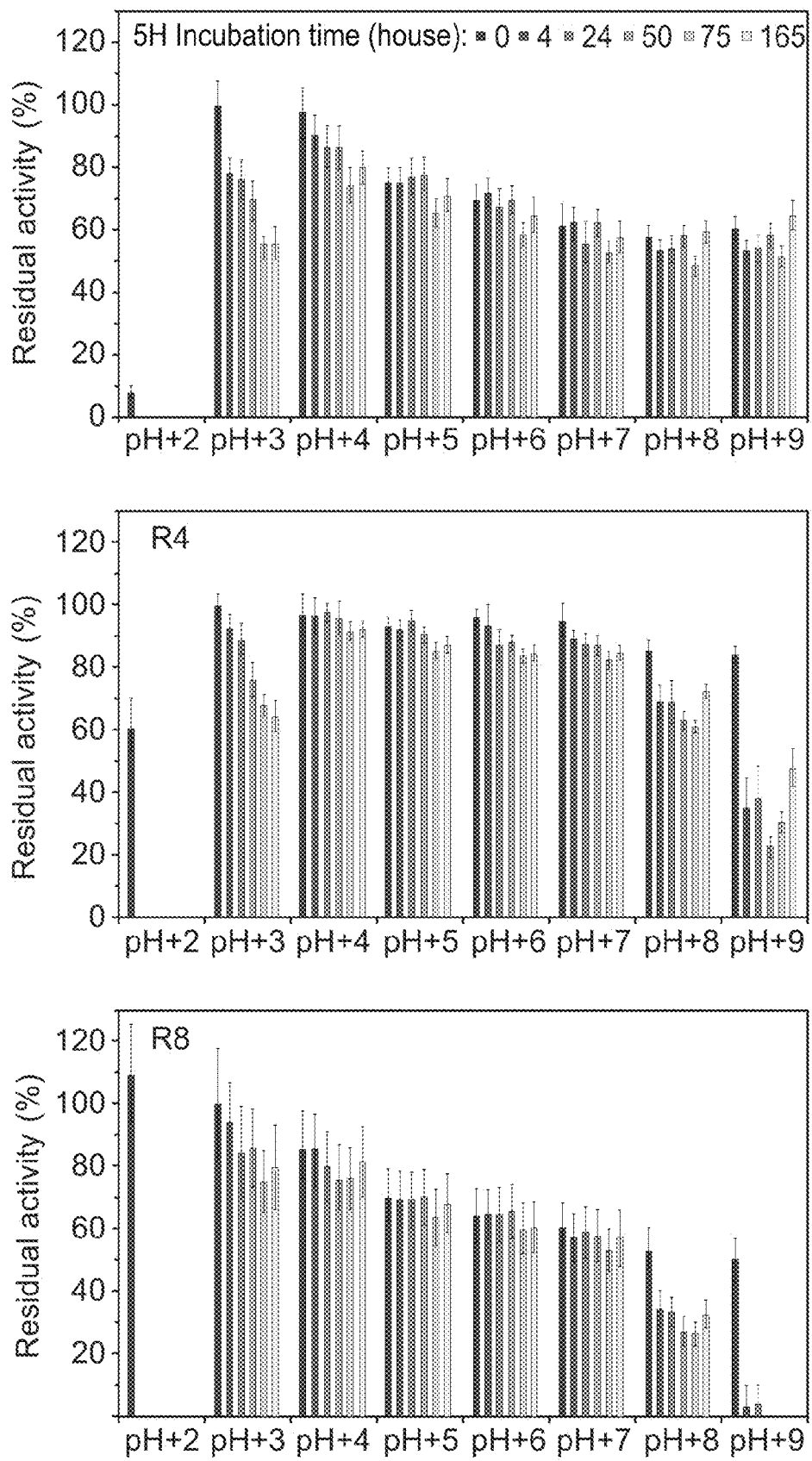
Figure 7A:
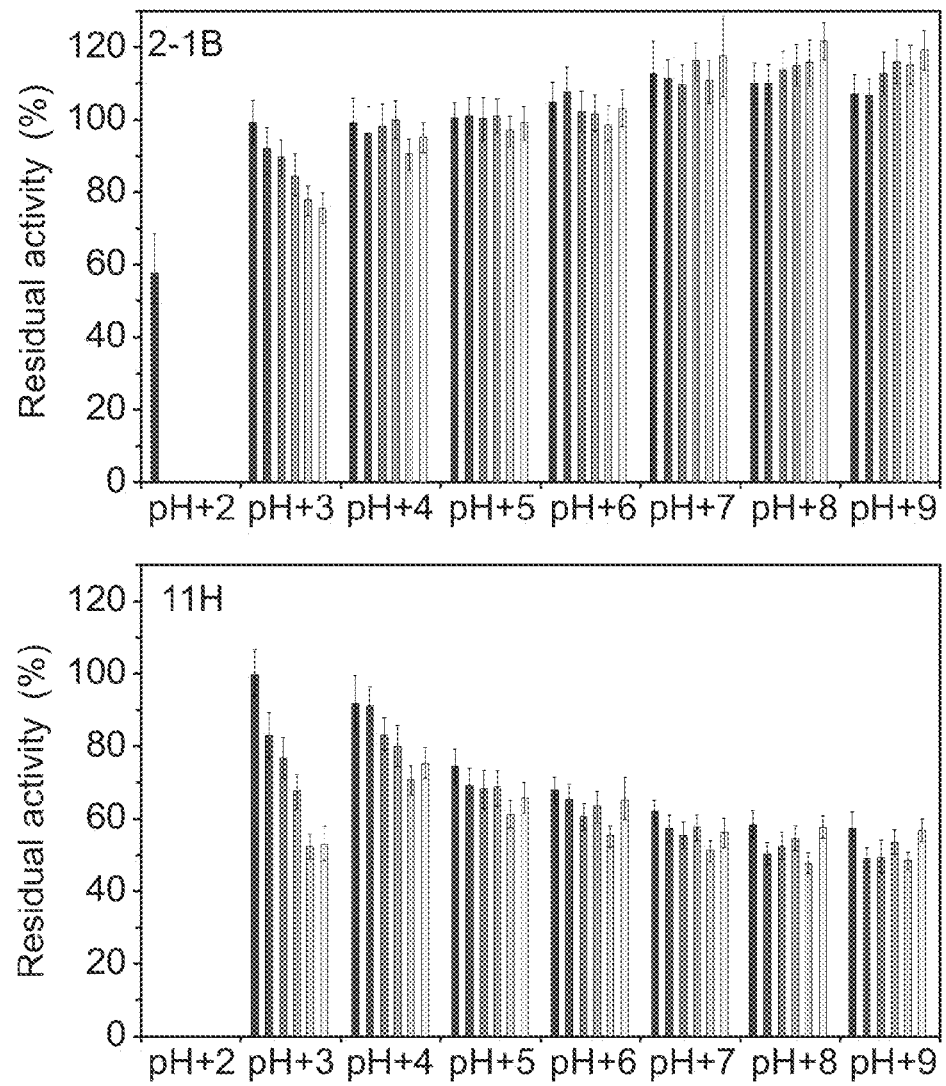

According to some embodiments of the invention, the peroxidase has a pH stability profile according to FIG. 7A.

According to some embodiments of the invention, the peroxidase is use in at least one of the following applications:
(i) bio-remediation;
(ii) pulp bleaching;
(iii) animal feed production;
(iv) biofuel production;
(v) dye bleaching;
(vi) laundering; or
(vii) skin or hair lightening.

According to an aspect of some embodiments of the present invention there is provided a polynucleotide comprising a nucleic acid sequence encoding the peroxidase enzyme described herein.

According to some embodiments of the invention, the peroxidase is codon-optimized for expression in a yeast cell.

According to an aspect of some embodiments of the present invention there is provided a yeast cell comprising the polynucleotide and/or protein of the peroxidase described herein.

According to some embodiments of the invention, the yeast cell is a *Saccharomyces cerevisiae* cell.

According to an aspect of some embodiments of the present invention there is provided a method of producing a peroxidase enzyme, the method comprising expressing in yeast the polynucleotide described herein, thereby producing the peroxidase enzyme.

According to some embodiments of the invention, the method further comprises isolating the peroxidase enzyme from the yeast or conditioned medium thereof.

According to an aspect of some embodiments of the present invention there is provided a culture comprising a biomass composition which comprises lignin and a population of yeast cells expressing at least one peroxidase enzyme described herein.

According to some embodiments of the invention, the culture is a silage.

According to some embodiments of the invention, the at least one peroxidase enzyme comprises the peroxidase enzyme having an amino acid sequence at least 85% identical to SEQ ID NO: 1 and the peroxidase enzyme having an amino acid sequence at least 85% identical to SEQ ID NO: 2.

According to some embodiments of the invention, the at least one peroxidase enzyme comprises the peroxidase enzyme having an amino acid sequence at least 85% identical to SEQ ID NO: 1 and the peroxidase enzyme having an amino acid sequence at least 85% identical to SEQ ID NO: 3.

According to some embodiments of the invention, the at least one peroxidase enzyme comprises the peroxidase enzyme having an amino acid sequence at least 85% identical to SEQ ID NO: 2 and the peroxidase enzyme having an amino acid sequence at least 85% identical to SEQ ID NO: 3.

According to some embodiments of the invention, the at least one peroxidase enzyme comprises the peroxidase enzyme having an amino acid sequence at least 85% identical to SEQ ID NO: 1, the peroxidase enzyme having an amino acid sequence at least 85% identical to SEQ ID NO: 2 and the peroxidase enzyme having an amino acid sequence at least 85% identical to SEQ ID NO: 3.

According to some embodiments of the invention, the culture further comprises yeast cells which express a peroxidase enzyme having an amino acid sequence at least 85% identical to SEQ ID NO: 7.

According to an aspect of some embodiments of the present invention there is provided a method of degrading lignin comprising contacting the lignin with at least one peroxidase enzyme described herein or with the cell described herein under conditions that allow the peroxidase enzyme to depolymerize the lignin, thereby degrading the lignin.

According to some embodiments of the invention, the lignin is comprised in lignocellulosic plant material.

According to some embodiments of the invention, the lignocellulolosic plant material is comprised in a woody material.

According to some embodiments of the invention, the lignocellulolosic plant material is comprised in a non-woody material.

According to some embodiments of the invention, the method further comprises contacting the lignin with at least one additional enzyme selected from the group consisting of a cellulose and a xylanase.

According to some embodiments of the invention, the method further comprises isolating at least one reaction product following the degrading.

According to some embodiments of the invention, the reaction product is a biofuel.

According to some embodiments of the invention, the biofuel is selected from the group consisting of ethanol, butanol and polylactic acid.

According to some embodiments of the invention, the reaction product is selected from the group consisting of vanillin, syringaldehyde and ferulic acid.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-D present key steps in the design of a naturally diverse set of VPs. (A) VP sequences were collected from different databases, a phylogenetic tree was constructed and twelve sequences that represent all branches were selected for diversification. (B) The selected sequences were modeled by trRosetta (Hiranuma et al., Nat. Commun. 12, 1340, 2021; Yang et al., Proc. Natl. Acad. Sci. U.S.A. 117, 1496-1503, 2020). For visualization, heme (red), manganese (pink) and calcium ions (blue) were superimposed from the VPL structure (PDB code: 3FJW). The surface-reactive tryptophan is presented in purple balls-and-sticks. (C) stability design calculations suggested dozens of mutations (yellow spheres). (D) In an experimental activity screen, the wild type proteins show negligible functional expression while the designs with the highest mutational load are highly active on the peroxidase substrate ABTS.

Figure 2A:
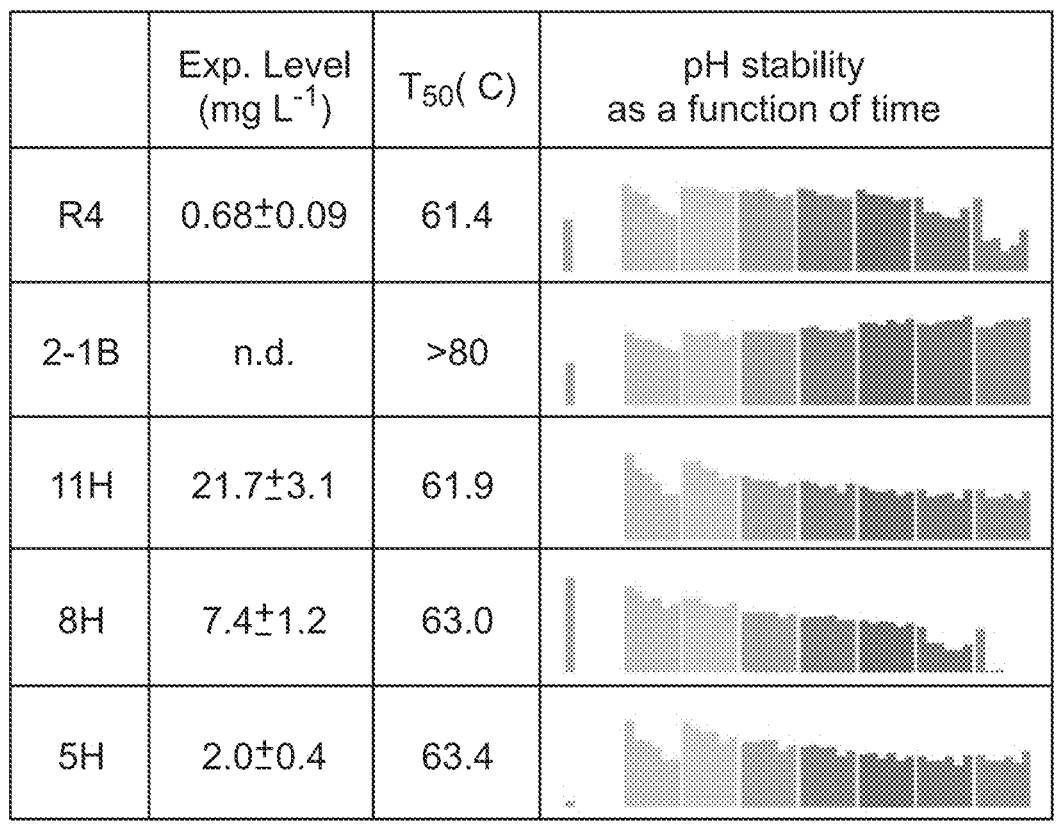
Figure 2A:
Figure 2B:
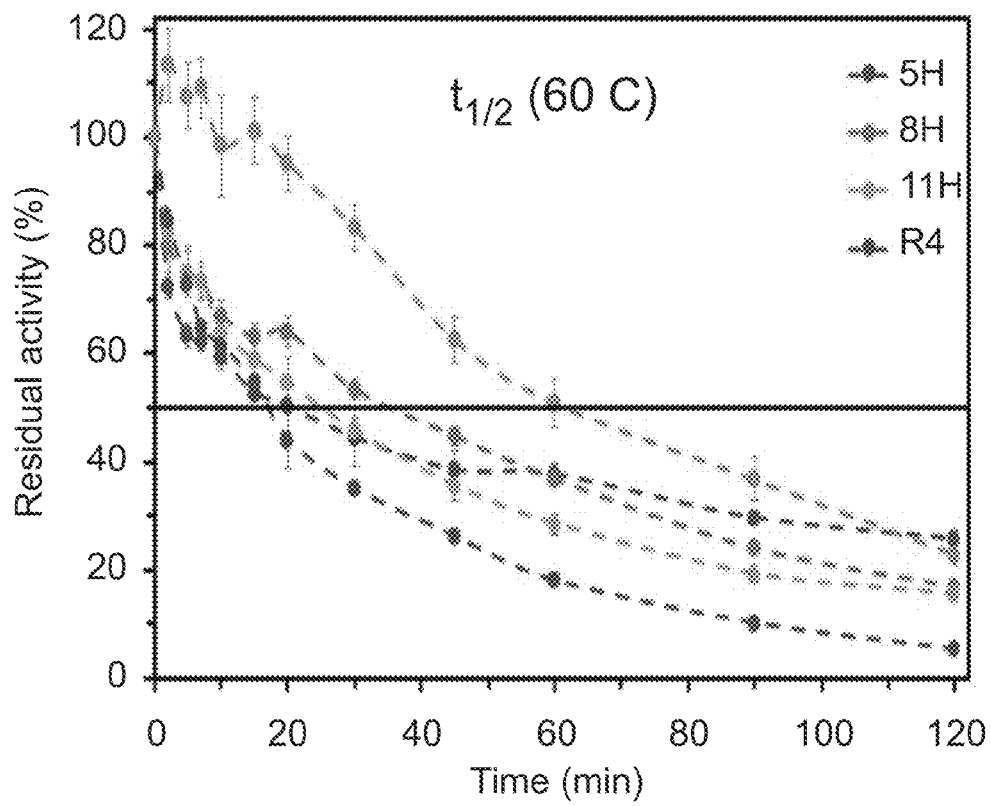
Figure 2C:
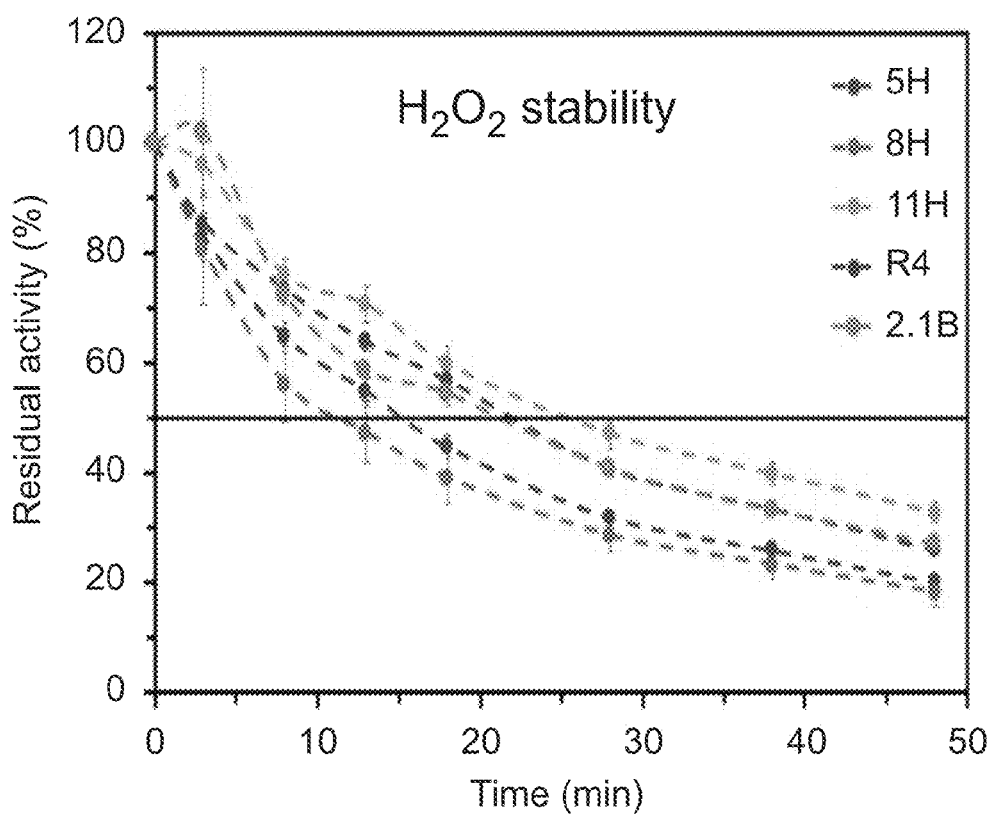

FIGS. 2A-C. Functional expression levels, thermal and pH stability in VP designs. (A) The expression levels were calculated using the initial activity at ABTS saturating concentrations in the supernatant immediately after growth and the ABTS kinetic values. Apparent Tso values were calculated based on the residual activity of enzymes incubated at different temperatures (see FIG. 6A). pH stability was assessed by incubation at pH ranging from 2-9, and measuring the residual activity at times 0, 4, 24, 50, 75 and 165 hours, compared to the activity at pH=3 at time zero (see FIG. 7A-B for complete data). (B) Kinetic thermostability ($t_{1/2}$) profiles were determined by incubating VP supernatants at 60° C. and measuring their residual activity at times 0-120 minutes, compared to the initial activity. (C) $H_2O_2$ stability ($t_{1/2}$) profiles were determined by incubating designs in $H_2O_2$ in a ratio of 1:3,000 and measuring their residual activity at times 0-48 minutes, compared to the initial activity. All the results are the means±S.D. of three independent experiments.

Figure 8:
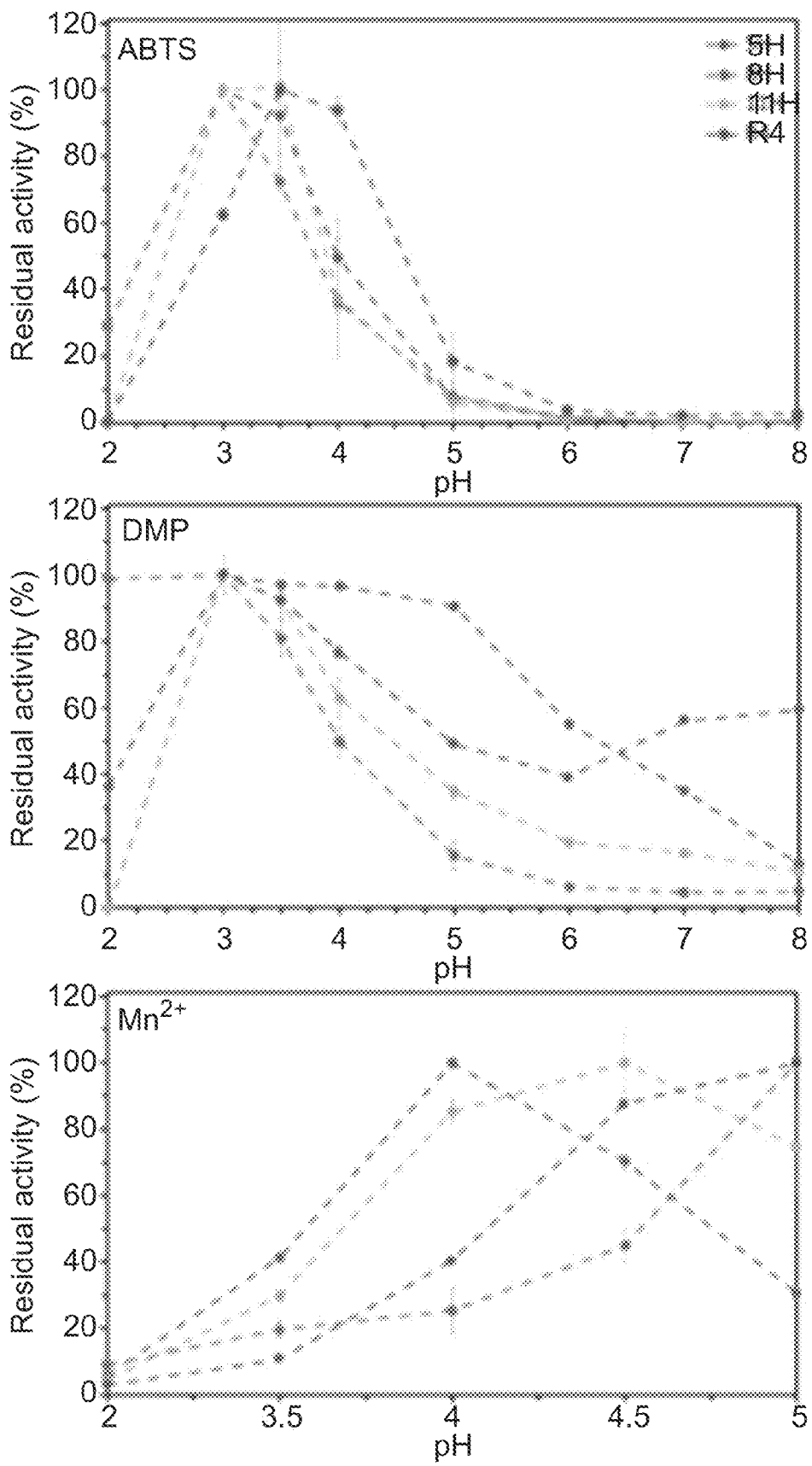
Figure 8:
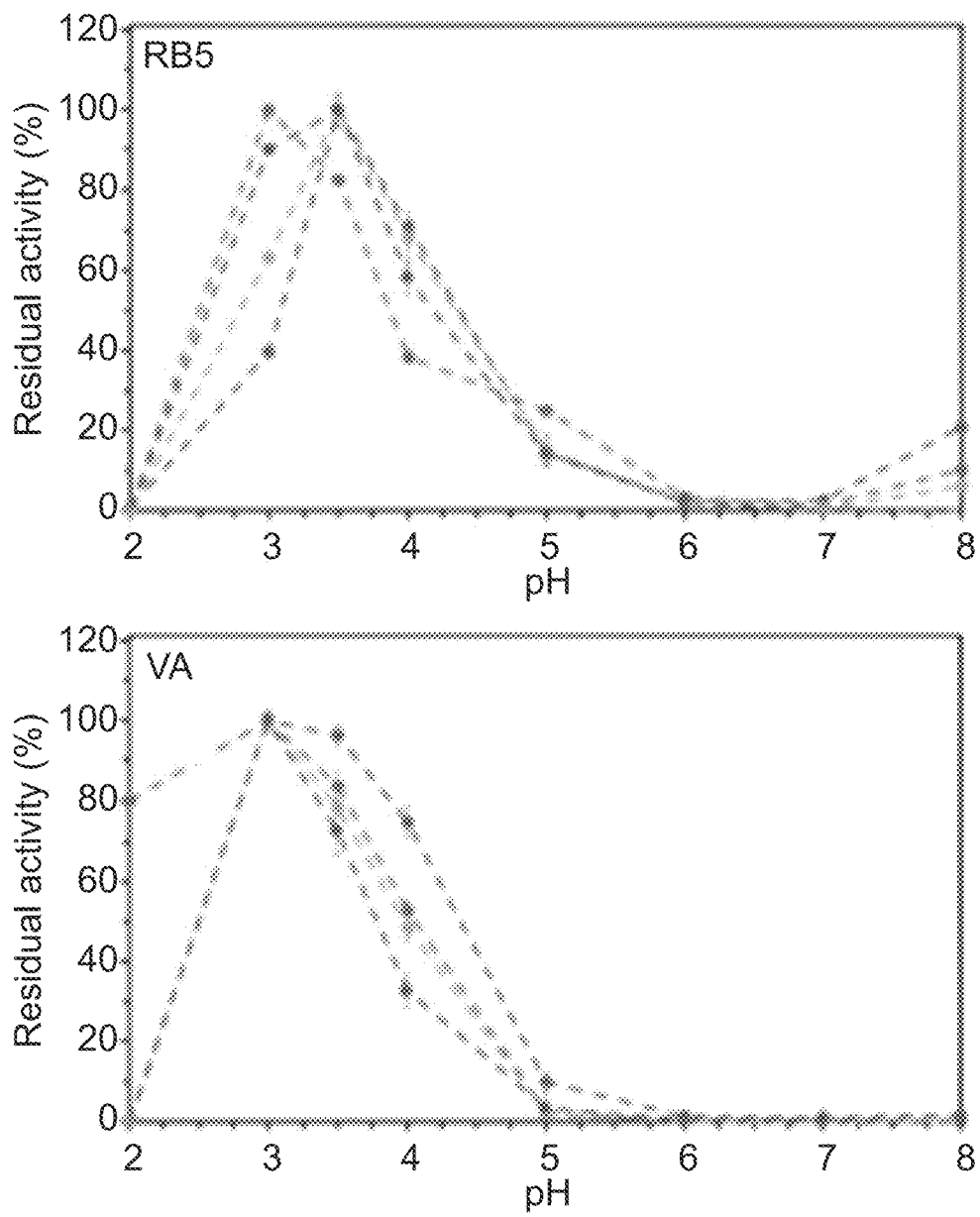

FIG. 3 presents high functional diversity among VP designs. For each VP (5H, 8H, 11H and R4) and substrate (ABTS, DMP, RB5, VA and $Mn^{2+}$), two kinetic parameters are shown, $K_M$ and $k_{cat}$ (in μM and $sec^{-1}$, respectively); bars are normalized to the larger value in each substrate (worst $K_M$ and best $k_{cat}$). For ABTS and DMP, light bars refer to the kinetic parameters of the low-efficiency site and the dark bars to the high-efficiency site; kinetic values are normalized separately for each (Table 4 shows all kinetic parameters). The best affinity (lowest $K_M$) and turnover number (highest $k_{cat}$) for each substrate are highlighted in bold. pH-dependent activity profiles are shown for each enzyme-substrate pair, and the bars are normalized to the activity at optimal pH for each such pair (FIG. 8 shows full activity plots).

FIGS. 4A-D. Structural basis for altered activity in VPs. (A) AlphaFold2 models of 5H, 8H and 11H are superimposed onto the VPL crystallographic structure (PDB entry 3FJW). All VP backbones are presented in gray cartoons, VPL calcium and manganese ions are in teal and pink spheres, respectively, and the heme group in pink sticks in all panels. Backbone segments that are unique for 8H are colored in purple. (B) Manganese-oxidation site. VPL and 8H residues that chelate manganese and vicinal residues are presented in gray and purple sticks, respectively. Significant variations are marked in arrows and their position identities and numbers are relative to PDB entry 3FJW in all panels. (C) Reactive surface tryptophanyl site. Tryptophan is presented in salmon sticks. VPL and 8H residues in the tryptophan vicinity are presented in gray and purple sticks, respectively. (D) Access channel to the heme-oxidation site. Guaiacol (GUA), which is chemically similar to DMP, from a VPL crystallographic structure (PDB entry 4G05) is presented in yellow sticks. VPL residues in the GUA vicinity are presented in gray. Mutations relative to VPL are presented in green, purple and orange sticks for 5H, 8H and 11H, respectively, and are marked in arrows.

FIGS. 5A-C presents accuracy of trRosetta models. (A) Four most reliable (top-ranked) models of a representative VP (VP5, gray), superimposed onto one another, demonstrate that most of the protein structural elements are converged, and small discrepancies occur only in peripheral loops (brown). (B) Best model of VP5 (gray) overlapped onto wildtype VPL crystal structure (PDB entry 3FJW; light green). VPL calcium and manganese ions are presented in blue and pink spheres, respectively, and the heme group in pink sticks. (C) close-up look onto VP5 residues that face all ligands and ions.

Figure 6A:
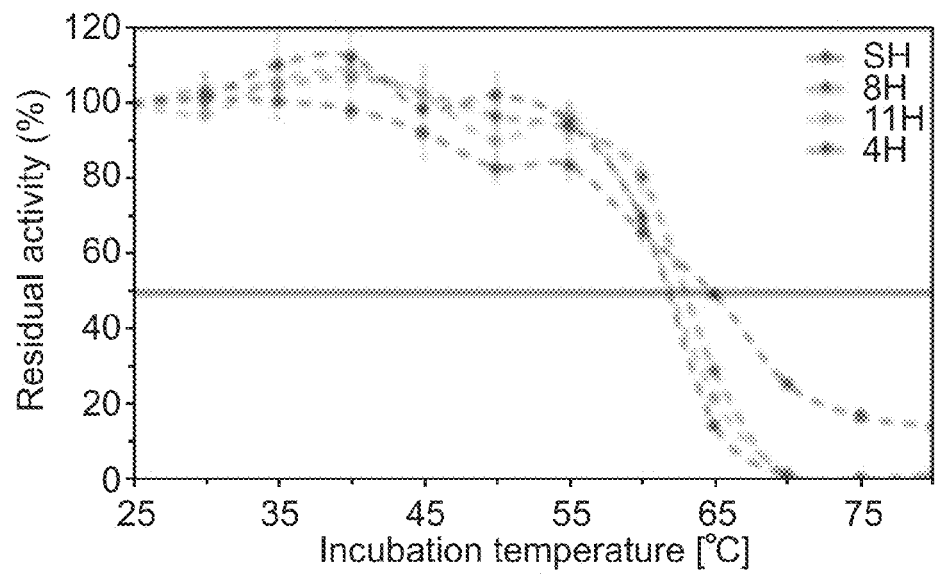
Figure 6B:
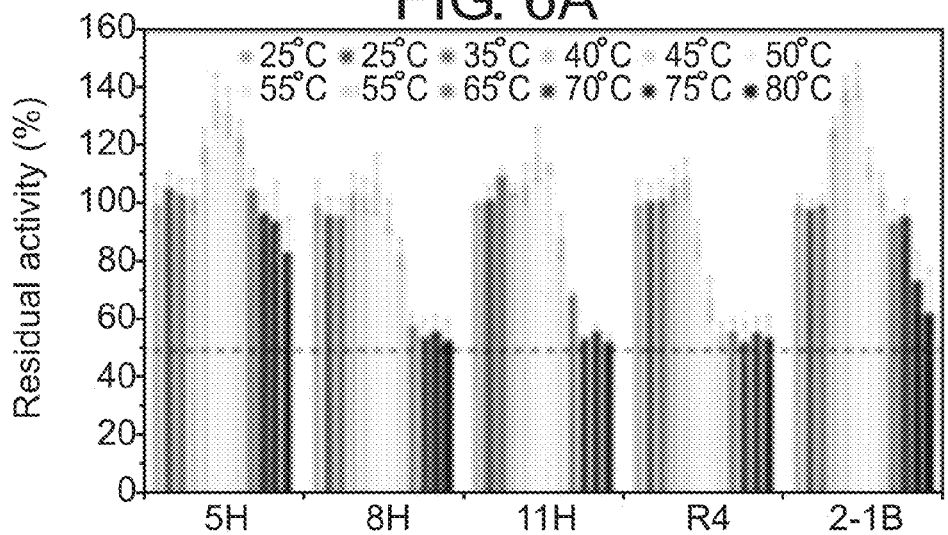
Figure 6C:
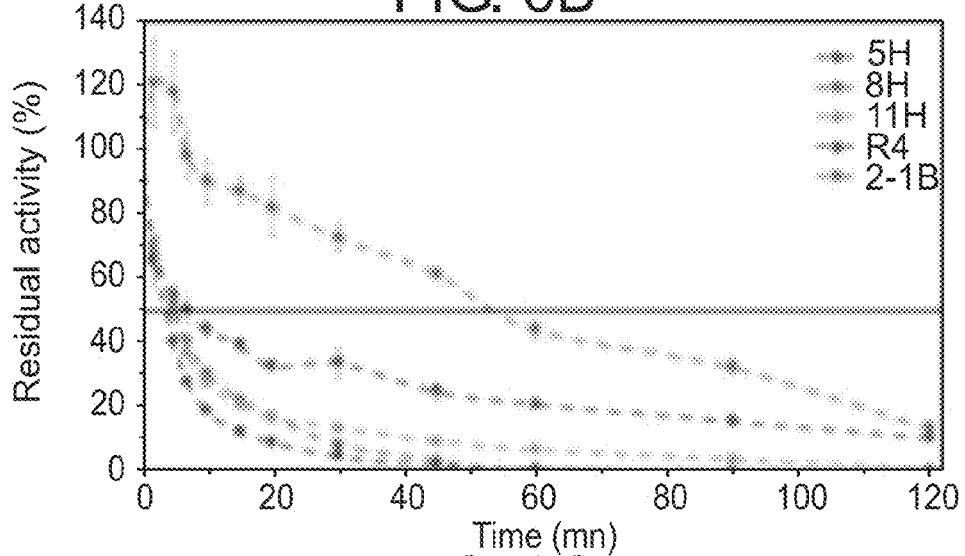

FIGS. 6A-C present thermal stabilities of selected VP variants (5H, 8H, 11H, VPL-R4 and 2-1B). VPs were incubated for (A) 15 or (B) 10 minutes at temperatures ranging from 30 to 80° C., and their residual 12 activity compared to the activity at 25° C. was measured. (C) kinetic thermostability ($t_{1/2}$) profiles were determined by incubation of VP supernatants at 65° C. and measuring their residual activity at times 0-120 minutes, compared to the activity at time zero.

Figure 7B:
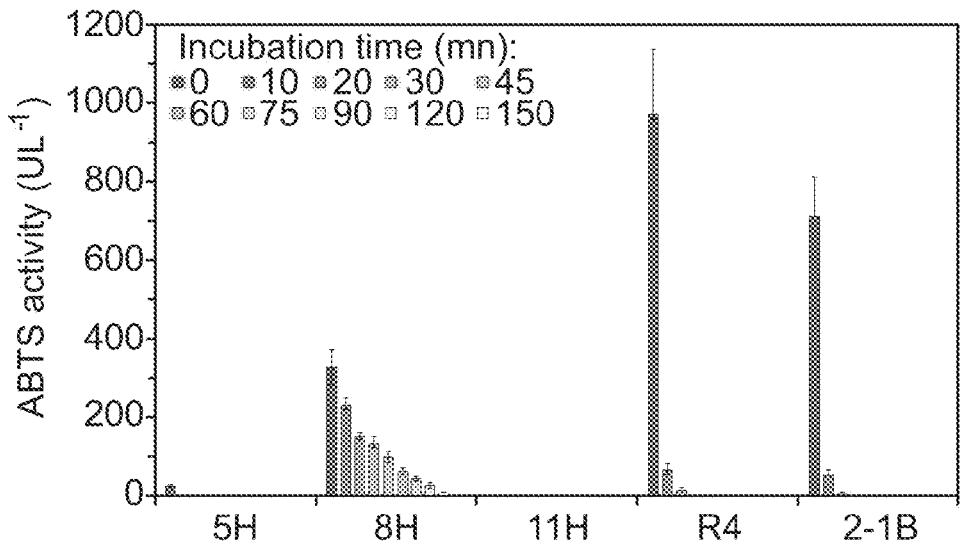

FIGS. 7A-B present pH stabilities of selected VP variants (5H, 8H, 11H, VPL-R4 and 2-1B). (A) VPs were incubated at pH ranging from 2-9 using 100 mM citrate-phosphate-borate buffer, and their residual activity at times 0-165 hours, compared to the activity at pH=3 at time zero, was measured. (B) VPs were incubated at 100 mM citrate-phosphate-borate buffer pH=2, and their residual activity at times 0-150 minutes, compared to time zero, was measured. All the results are the means±S.D. from three independent experiments.

FIG. 8 represents pH activity profiles of selected VP variants with versatile substrates. Purified 5H, 8H, 11H and R4 assayed for activity at range of pHs (pHs 2-9 to all substrates but $Mn^{2+}$, in which was tested at pH range of 3-5), using appropriate substrate concentrations ([S]>>[E] but with linear response): ABTS, DMP, $Mn^{2+}$, VA and RB5. VPs activity was normalized to the activity at optimal pH for each protein-substrate pair. All the results are the means±S.D. from three independent experiments.

FIGS. 9A-C. Sequence alignment of 5H (SEQ ID NO: 1; FIG. 9A), 8H (SEQ ID NO: 2: FIG. 9B) and 11H (SEQ ID NO: 3; FIG. 9C) to their wildtype progenitor (SEQ ID NO: 4 for 5WT; SEQ ID NO: 5 for 8WT and SEQ ID NO: 6 for 11WT). Mutated positions are highlighted in green. Design in positions highlighted in gray were disallowed due to: proximity to one of the active sites or structural calcium ions, putative disulfide-bond forming cysteines or structural inconsistency in the best five models calculated by trRosetta. Mutations calculated by the proprietary algorithm in positions highlighted in yellow were omitted after visual inspection due to one of the following reasons: low homologous-sequence data in the mutation region (PSSM with less than 10 sequences), formation or depletion of possible N-glycosylation site, radical mutation in the protein core (large hydrophobic to small hydrophobic, hydrophilic to hydrophobic substitutions, etc.), mutation in the heme's substrate pocket and mutation in possible contact with structural inconsistent regions.

DESCRIPTION OF SPECIFIC EMBODIMENTS OF THE INVENTION

The present invention, in some embodiments thereof, relates to recombinant versatile peroxidases and uses thereof.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

White-rot fungi secrete a repertoire of high-redox potential oxidoreductases to efficiently decompose lignin. Of these enzymes, versatile peroxidases (VPs) are the most promiscuous biocatalysts. VPs are attractive enzymes for research and industrial use, but their recombinant production is extremely challenging. To date, only a single VP has been structurally characterized and optimized for recombinant functional expression, stability, and activity.

The method disclosed herein addresses the challenge by providing recombinant VPs, obtained through computational design, having unexpected stability and activity. Specifically, thirty six VPs were designed encoding as many as 43 mutations relative to the wild type enzymes. Four of the designs were shown to be functionally expressed in yeast whereas their wild type parents were not. Furthermore, three of these designs exhibited substantial and useful diversity in their reactivity profiles and tolerance to environmental conditions (see Table 4).

Thus, according to a first aspect of the present invention there is provided a peroxidase enzyme comprising:
(i) an amino acid sequence at least 85% identical to SEQ ID NO: 1; and
(ii) mutations set forth in A11S, V15T, A17S, A19E, P26D, D38G, A40Q, D44Q, T79I, V81T, E91D, P98S, A101Q, G115A, K138T, A140P, I143P, T152S, I153V, D161A, V166S, S167P, E187P, I205F, I214T, S215T, H223P, Q227K, K231P, D246P, S249A, T256V, S267R, A282D, A294P, A295P, V297T, G318A, A319P, A322T, G324P, V330P and R335P, wherein the coordinates correspond to the SEQ ID NO: 1;
wherein the peroxidase enzyme is characterized by increased yield when expressed in yeast cells as compared to wild-type peroxidase enzyme having an amino acid sequence as set forth in SEQ ID NO: 4.

According to another aspect of the present invention, there is provided a peroxidase enzyme comprising:
(i) an amino acid sequence at least 85% identical to SEQ ID NO: 2; and
(ii) mutations set forth in R4P, M5S, E34T, G59A, T65W, A67Q, V85I, V95I, P104H, I107Q, T125V, S135P, S141P, D143P, S161Q, S164A, S167A, D172S, D229Q, A247L, S249A, S252P, R265Q, A266D, L269Q, A270S, E273A, G274A, A288S, T290I, A299P, T300P, S323D, A325P, S330P, A333P, A335P and A341P, wherein the coordinates correspond to the SEQ ID NO: 2;
wherein the peroxidase enzyme is characterized by increased yield when expressed in yeast cells as compared to wild-type peroxidase enzyme having an amino acid sequence as set forth in SEQ ID NO: 5.

According to still another aspect of the present invention, there is provided a peroxidase enzyme comprising:
(i) an amino acid sequence at least 85% identical to SEQ ID NO: 3; and
(ii) mutations set forth in A11S, V15T, A17S, P26D, I27L, L28R, E29D, E40Q, T74I, P78T, V80L, A100Q, K137T, A139P, I142D, T151S, T153D, D157A, G160A, A165S, A166P, E186P, S187T, S214L, S218T, H222P, A230P, S245P, S248A, Q279V, A280R, A294P, K298T, V306T, A321T, A323P and A331S, wherein the coordinates correspond to the SEQ ID NO: 3;
wherein the peroxidase enzyme is characterized by increased yield when expressed in yeast cells as compared to wild-type peroxidase enzyme having an amino acid sequence as set forth in SEQ ID NO: 6.

The peroxidase of the above described aspects are versatile peroxidases.

The term "versatile peroxidase" (also referred to as VP), refers to a heme peroxidase which is classified under EC 1.11.1.16 and which requires $H_2O_2$ as an oxidant.

Exemplary amino acid sequences of wild-type versatile peroxidases include SEQ ID NO: 4 and 6 (*Pleurotus ostreatus*); SEQ ID NO: 5 (*Ganoderma* sp. 10597_SS1) and SEQ ID NO: 8 (*Pleurotus eryngii*).

As used herein, the term "protein" is interchangeably used with the term "polypeptide". According to teachings of the invention, alterations are made to the wild-type sequence to produce the peroxidase having an enzymatic activity for at least one of the same substrates as the wild type protein.

The term "variant", in the structural sense, means a polypeptide derived from a wild type versatile peroxidase comprising an alteration, i.e., a substitution, insertion, and/or deletion, at one or more (several) positions.

A substitution means a replacement of an amino acid occupying a position with a different amino acid; a deletion means removal of an amino acid occupying a position; and an insertion means adding 1-3 amino acids adjacent to an amino acid occupying a position. The altered polypeptide (variant) can be obtained through human intervention by modification of the polynucleotide sequence encoding the wild type protein.

According to a specific embodiment, the alteration is a substitution.

According to a specific embodiment, the alteration comprises a plurality of modifications (e.g. substitutions) e.g., at least 1% of all the amino acids of the protein, at least 2% of all the amino acids of the protein, at least 3% of all the amino acids of the protein, at least 4% of all the amino acids of the protein, at least 5% of all the amino acids of the protein, at least 6% of all the amino acids of the protein, at least 7% of all the amino acids of the protein, at least 8% of all the amino acids of the protein, at least 9% of all the amino acids of the protein, at least 10% of all the amino acids of the protein, at least 15% of all the amino acids of the protein, at least 20% of all the amino acids of the protein.

According to another embodiment, no more than 20% of all the amino acids of the protein are modified (e.g. substituted), no more than 30% of all the amino acids of the protein are modified, no more than 40% of all the amino acids of the protein are modified, no more than 50% of all the amino acids of the protein are modified.

According to alternative embodiments, the protein variant comprises an amino acid sequence which is at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to SEQ ID NO:1, as determined using the BestFit software of the Wisconsin sequence analysis package, utilizing the Smith and Waterman algorithm, where gap weight equals 50, length weight equals 3, average match equals 10 and average mismatch equals-9. Of note, the percentage of identity refers to global identity over the peroxidase protein sequence.

According to another embodiment, the protein variant comprises an amino acid sequence which is at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to SEQ ID NO: 2, as determined using the BestFit software of the Wisconsin sequence analysis package, utilizing the Smith and Waterman algorithm, where gap weight equals 50, length weight equals 3, average match equals 10 and average mismatch equals-9.

According to another embodiment, the protein variant comprises an amino acid sequence which is at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to SEQ ID NO: 3, as determined using the BestFit software of the Wisconsin sequence analysis package, utilizing the Smith and Waterman algorithm, where gap weight equals 50, length weight equals 3, average match equals 10 and average mismatch equals-9.

According to a specific embodiment, the protein is at least 95% identical to SEQ ID NO: 1, 2 or 3.

According to a specific embodiment, the protein is at least 99% identical to SEQ ID NO: 1, 2 or 3.

According to a specific embodiment, the protein consists of the amino acid sequence set forth in SEQ ID NO: 1, 2 or 3.

According to a specific embodiment, the protein variant exhibits increased yield when compared to the wild type protein when expressed in yeast.

As used herein "increased yield" refers to at least 5 fold, 10 fold, 15 fold, 20 fold, 25 fold, 30 fold, 40 fold, 50 fold, 70 fold, 100 fold, 500 fold, 1000 fold higher expression of the variant than that of wild type protein.

The variants described herein comprise enzymatic activity towards at least one, at least two, at least three, at least four or all of the following substrates: 2,2'-azino-bis(3-ethylbenzothiazoline-6-sulfonic acid (ABTS), 2,6-dimethoxyphenol (DMP), veratryl alcohol (VA), reactive black 5 (RB5) and $Mn^{2+}$. Enzymatic activity may be determined as described in the Examples section, herein below.

According to a specific embodiment, the variant having an amino acid sequence at least 85% identical to SEQ ID NO: 1 shows enzymatic activity similar or higher to the enzymatic activity of 5H towards at least one of, at least two of, at least three of, at least four of, or each of 2,2'-azino-bis(3-ethylbenzothiazoline-6-sulfonic acid (ABTS), 2,6-dimethoxyphenol (DMP), veratryl alcohol (VA), reactive black 5 (RB5) and $Mn^{2+}$ as shown in Table 4, where similar refers to having a similar Km or Kcat value (e.g. of the same order or being of a number refers to ±10%) under identical experimental conditions. Preferably, the variant having an amino acid sequence at least 85% identical to SEQ ID NO: 1 shows enzymatic activity similar or higher to the enzymatic activity 5H shows towards VA. Preferably, the variant having an amino acid sequence at least 85% identical to SEQ ID NO: 1 shows a stability under acidic pH which is similar or higher than the stability 5H shows under the acidic pH. For example, the variant having an amino acid sequence at least 85% identical to SEQ ID NO: 1 shows a stability as set forth for 5H in FIG. 7A.

In another embodiment, the variant having an amino acid sequence at least 85% identical to SEQ ID NO: 1 is capable of being functionally expressed (i.e. capable of carrying out at least one of the enzymatic reactions detailed above) in yeast.

According to a specific embodiment, the variant having an amino acid sequence at least 85% identical to SEQ ID NO: 2 shows enzymatic activity similar or higher to the enzymatic activity of 8H towards at least one of, at least two of, at least three of, at least four of, or each of 2,2'-azino-bis(3-ethylbenzothiazoline-6-sulfonic acid (ABTS), 2,6-dimethoxyphenol (DMP), veratryl alcohol (VA), reactive black 5 (RB5) and $Mn^{2+}$ as shown in Table 4, where similar refers to having a similar Km or Kcat value (e.g. of the same order or being of a number refers to ±10%). Preferably, the variant having an amino acid sequence at least 85% identical to SEQ ID NO: 2 shows a stability under acidic pH and neutral pH which is similar to or higher than the stability 5H shows under the acidic pH and neutral pH. For example, the variant having an amino acid sequence at least 85% identical to SEQ ID NO: 2 shows a stability as set forth for 8H in FIG. 7A.

In another embodiment, the variant having an amino acid sequence at least 85% identical to SEQ ID NO: 2 is capable of being functionally expressed (i.e. capable of carrying out at least one of the enzymatic reactions detailed above) in yeast.

According to a specific embodiment, the variant having an amino acid sequence at least 85% identical to SEQ ID NO: 3 shows enzymatic activity similar or higher to the enzymatic activity of 11H towards at least one of, at least two of, at least three of, at least four of, or each of 2,2'-azino-bis(3-ethylbenzothiazoline-6-sulfonic acid (ABTS). 2,6-dimethoxyphenol (DMP), veratryl alcohol (VA), reactive black 5 (RB5) and $Mn^{2+}$ as shown in Table 4, where similar refers to having a similar Km or Kcat value (e.g. of the same order or being of a number refers to +10%). Preferably, the variant having an amino acid sequence at least 85% identical to SEQ ID NO: 3 shows enzymatic activity similar or higher to the enzymatic activity 11H shows towards $H_2O_2$. Preferably, the variant having an amino acid sequence at least 85% identical to SEQ ID NO: 3 shows a stability under acidic pH which is similar or higher than the stability 11H shows under the acidic pH. For example, the variant having an amino acid sequence at least 85% identical to SEQ ID NO: 3 shows a stability as set forth for 11H in FIG. 7A.

In another embodiment, the variant having an amino acid sequence at least 85% identical to SEQ ID NO: 3 is capable of being functionally expressed (i.e. capable of carrying out at least one of the enzymatic reactions detailed above) in yeast.

Thus, according to an aspect of the invention, there is provided a method of producing a peroxidase enzyme, the method comprising expressing in yeast a nucleic acid sequence encoding the protein variant as described herein, thereby producing the peroxidase enzyme.

Accordingly, there is provided a polynucleotide comprising a nucleic acid sequence encoding the protein variant as described herein.

In one embodiment, the nucleic acid sequence is codon-optimized for expression in yeast.

Codon degeneracy refers to the nature in the genetic code permitting variation of the nucleotide sequence without effecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

Thus, codons may be optimized for expression based on codon usage in the selected host, as is known to one skilled in the art.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA.

To express exogenous nucleic acid sequences in cells, a polynucleotide sequence encoding the protein variant is preferably ligated into a nucleic acid construct suitable for yeast cell expression. Such a nucleic acid construct includes a promoter sequence for directing transcription of the polynucleotide sequence in the cell in a constitutive or inducible manner.

The present invention contemplates yeast cells which co-express the peroxidases described herein. Thus, a single yeast cell can express a peroxidase having an amino acid sequence at least 85% identical to SEQ ID NO: 1 and the peroxidase having an amino acid sequence at least 85% identical to SEQ ID NO: 2. Alternatively, a single yeast cell can express a peroxidase having an amino acid sequence at least 85% identical to SEQ ID NO: 1 and the peroxidase having an amino acid sequence at least 85% identical to SEQ ID NO: 3. Alternatively, a single yeast cell can express a peroxidase having an amino acid sequence at least 85% identical to SEQ ID NO: 2 and the peroxidase having an amino acid sequence at least 85% identical to SEQ ID NO: 3. The yeast cells may further express a peroxidase having an amino acid sequence at least 85% identical to SEQ ID NO: 7.

Alternatively, the present invention contemplates compositions comprising at least two of the isolated peroxidases described herein. Thus, a single composition can comprise a peroxidase having an amino acid sequence at least 85% identical to SEQ ID NO: 1 and the peroxidase having an amino acid sequence at least 85% identical to SEQ ID NO: 2. Alternatively, a single composition can comprise a peroxidase having an amino acid sequence at least 85% identical to SEQ ID NO: 1 and the peroxidase having an amino acid sequence at least 85% identical to SEQ ID NO: 3. Alternatively, a single composition can comprise a peroxidase having an amino acid sequence at least 85% identical to SEQ ID NO: 2 and the peroxidase having an amino acid sequence at least 85% identical to SEQ ID NO: 3. The composition may further comprise a peroxidase having an amino acid sequence at least 85% identical to SEQ ID NO: 7.

The present invention further contemplates a cell based consortium comprising a first yeast cell that expresses a peroxidase having an amino acid sequence at least 85% identical to SEQ ID NO: 1 and a second yeast cell comprising the peroxidase having an amino acid sequence at least 85% identical to SEQ ID NO: 2. Alternatively, the cell based consortium can comprise a first yeast cell expressing a peroxidase having an amino acid sequence at least 85% identical to SEQ ID NO: 1 and a second yeast cell expressing the peroxidase having an amino acid sequence at least 85% identical to SEQ ID NO: 3. Alternatively, the cell based consortium can comprise a first yeast cell expressing a peroxidase having an amino acid sequence at least 85% identical to SEQ ID NO: 2 and a second yeast cell expressing a peroxidase having an amino acid sequence at least 85% identical to SEQ ID NO: 3. The cell consortium can also include cells expressing a peroxidase having an amino acid sequence at least 85% identical to SEQ ID NO: 7.

According to the present invention the yeast host cell can be, for example, from the genera *Saccharomyces. Kluyveromyces. Candida, Pichia, Schizosaccharomyces, Hansenula, Kloeckera, Schwanniomyces*, and *Yarrowia*. Yeast species as host cells can include, for example, *S. cerevisiae, S. bulderi, S. barnetti, S. exiguus, S. uvarum, S. diastaticus, K. lactis, K. marxianus*, or *K. fragilis*. In some embodiments, the yeast is selected from the group consisting of *Saccharomyces cerevisiae, Schizzosaccharomyces pombe, Candida albicans, Pichia pastoris, Pichia stipitis. Yarrowia Hpolytica, Hansenula polymorpha, Phaffia rhodozyma, Candida utilis, Arxula adeninivorans, Debaryomyces hansenii, Debaryomyces polymorphus. Schizosaccharomyces pombe* and *Schwanniomyces occidentalis*. In one particular embodiment, the yeast is *Saccharomyces cerevisiae*. The selection of an appropriate host is deemed to be within the scope of those skilled in the art from the teachings herein.

Any suitable promoter to drive gene expression in the host cells of the invention may be used.

In some embodiments, promoter regions from the *S. cerevisiae* genes PGK1, ENO1, TDH3, TDH2, TDH1, ENO2, GPM1, TPI1, GAC1, GETS, GLC7, GSH1, GSH2, HSF1, HSP12, LCB5, LRE1, LSP1, NBP2, PDC1, PIL1, PIM1, SGT2, SLG1, WHI2, WSC2, WSC3, WSC4, YAP1, YDC1, ESP 104, HSP26, ENA1, MSN2, MSN 4, SIP 2, SIP 4, SIP 5, DPL1, IRS4, KOG1, PEP 4, HAP4, PRB1, TAX4, ZPR1, ATG1, ATG2, ATG10, ATG11, ATG12, ATG13, ATG14, ATG15, ATG16, ATG17, ATG18, and ATG19 may be used. In addition, the expression vectors may contain one or more selectable marker genes to provide a phenotypic trait for selection of transformed host cells such as URA3, HIS3, LEU2, TRP1, LYS2 or ADE2, dihydrofolate reductase, neomycin (G418) resistance or zeocin resistance for eukaryotic cell culture, or tetracycline or ampicillin resistance in *E. coli*.

The expression vector may also contain a ribosome binding site for translation initiation and/or a transcription terminator. The vector may also include appropriate sequences for amplifying expression, or may include additional regulatory regions.

According to embodiments of the present invention, the peroxidase enzymes can be either tethered or secreted.

As used herein, a protein is "tethered" to an organism's cell surface if at least one terminus of the protein is bound, covalently and/or electrostatically for example, to the cell membrane or cell wall. It will be appreciated that a tethered protein can include one or more enzymatic regions that can be joined to one or more other types of regions at the nucleic acid and/or protein levels (e.g., a promoter, a terminator, an anchoring domain, a linker, a signaling region, etc.). While the one or more enzymatic regions may not be directly bound to the cell membrane or cell wall (e.g., such as when binding occurs via an anchoring domain), the protein is nonetheless considered a "tethered enzyme" according to the present specification. Tethering can, for example, be accomplished by incorporation of an anchoring domain into a recombinant protein that is heterologously expressed by a cell, or by prenylation, fatty acyl linkage, glycosyl phosphatidyl inositol anchors or other suitable molecular anchors which may anchor the tethered protein to the cell membrane or cell wall of the host cell. A tethered protein can be tethered at its amino terminal end or optionally at its carboxy terminal end.

As used herein, "secreted" refers to being released into the extracellular milieu, for example into the media. Although tethered proteins may have secretion signals as part of their immature amino acid sequence, they are maintained as attached to the cell surface, and do not fall within the scope of secreted proteins as used herein.

As used herein, "flexible linker sequence" refers to an amino acid sequence which links two amino acid sequences, for example, a cell wall anchoring amino acid sequence with an amino acid sequence that contains the desired enzymatic activity. The flexible linker sequence allows for necessary freedom for the amino acid sequence that contains the desired enzymatic activity to have reduced steric hindrance with respect to proximity to the cell and may also facilitate proper folding of the amino acid sequence that contains the desired enzymatic activity.

In some embodiments of the present invention, the tethered peroxidase enzymes are tethered by a flexible linker sequence linked to an anchoring domain. In some embodiments, the anchoring domain is of CWP2 (for carboxy terminal anchoring) or FLO1 (for amino terminal anchoring) from S. cerevisiae.

In some embodiments, heterologous secretion signals may be added to the expression vectors of the present invention to facilitate the extra-cellular expression of the peroxidase variants. In some embodiments, the heterologous secretion signal is the S. cerevisiae Invertase signal. In yet other embodiments, the heterologous secretion signal is the S. cerevisiae AF mating signal.

The expression of a heterologous stretch of amino acids (peptide tag, referred to herein as "tag") or a large polypeptide (fusion partner) in tandem with the desired protein, in this case the peroxidase variant, to form a chimeric protein is contemplated by the present inventors to aid in isolation.

Thus, according to an embodiment of the invention, the protein is an in-frame fusion with a heterologous tag, not naturally present in the peroxidase.

Peptide tags are less likely to interfere when fused to the protein. Vectors are available that allow positioning of the tag on either the N-terminal or the C-terminal end (the latter option being advantageous when a signal peptide is positioned at the N-terminal end for secretion of the recombinant protein). Common examples of small peptide tags are the poly-Arg-, FLAG-, poly-His-, c-Myc-, S-, and Strep II-tags. Since commercial antibodies are available for all of them, the tagged recombinant protein can be detected by Western blot along expression trials, which is helpful when the levels of the desired proteins are not high enough to be detected by SDS-PAGE. Also, tags allow for one-step affinity purification, as resins that tightly and specifically bind the tags are available. For example. His-tagged proteins can be recovered by immobilized metal ion affinity chromatography using $Ni^{2+}$ or $Co^{2+}$-loaded nitrilotriacetic acid-agarose resins (see the Examples section which follows), while anti-FLAG affinity gels (Sigma-Aldrich) are used for capturing FLAG fusion proteins.

On the other hand, adding a non-peptide fusion partner has the extra advantage of working as solubility enhancers. The most popular fusion tags are the maltose-binding protein (MBP), N-utilization substance protein A (NusA), thioredoxin (Trx), glutathione S-transferase (GST), ubiquitin and SUMO, calcium binding protein Fh8

A different group of fusion tags which are also envisaged herein are stimulus-responsive tags, which reversibly precipitate out of solution when subjected to the proper stimulus. The addition of β roll tags to a recombinant protein allows for its selective precipitation in the presence of calcium. The final products present a high purity and the precipitation protocol only takes a couple of minutes. These techniques represent an alternative to conventional chromatography-based purification methods and can save production costs, especially in large-scale settings.

According to some embodiments of the invention, affinity chromatography can be used to recover the protein from the expression system following expression.

Poly-His, MBP or GST can be used to purify the fused protein by affinity chromatography, as poly-His binds to nickel column, MBP binds to amylose-agarose and GST to glutathione-agarose. MBP is present in the pMAL series of vectors from NEB and GST in the pGEX series (GE). A peptide tag is preferably added to the fusion partner-containing protein if an affinity chromatography step is needed in the purification scheme. MBP and GST bind to their substrates non-covalently. On the contrary, the HaloTag7 (Promega) is based on the covalent capture of the tag to the resin, making the system fast and highly specific.

According to another embodiment, the protein variant is expressed tagless, i.e., without a tag and conventional chromatography based purification methods are used for isolating the protein. Alternatively, the tag is removed following expression and purification.

Thus, embodiments of the invention envisage isolating the protein from the yeast or conditioned medium thereof once sufficient levels are achieved.

According to a specific embodiment the tag is removed to avoid interference with protein activity and/or structure, but on the other embodiments they can be left in place even for crystallographic studies. Tags can be eliminated by either enzymatic cleavage or chemical cleavage.

Recovery of the recombinant protein variant is effected following an appropriate time in culture. The phrase "recovering the recombinant polypeptide" refers to collecting the whole fermentation medium containing the polypeptide and need not imply additional steps of separation or purification. Alternatively the protein can be recovered from the intracellular space (e.g., cytosol) following lysis and optionally sonication). Notwithstanding the above, proteins of some embodiments of the invention can be purified using a variety of standard protein purification techniques, such as, but not limited to, affinity chromatography, ion exchange chromatography, filtration, electrophoresis, hydrophobic interaction chromatography, filtration chromatography, reverse phase chromatography, concanavalin A chromatography, chromatofocusing and differential solubilization.

Since the peroxidases disclosed herein are so functionally promiscuous, they have a myriad of uses. The choice of which particular enzyme to use depends on the particular function required and the conditions in which the reaction takes place.

In one embodiment, the peroxidase is used to degrade lignin.

Thus, according to another aspect of the present invention there is provided a method of degrading lignin comprising contacting the lignin with at least one peroxidase enzyme described herein or with a yeast cell which expresses at least one peroxidase enzyme described herein under conditions that allow the peroxidase enzyme to depolymerize the lignin, thereby degrading the lignin.

The lignin is typically comprised in lignocellulosic biomass. The biomass composition may be living or dead. The lignocellulosic material comprises lignin and cellulose (and optionally hemicellulose, mannan and other materials commonly found in biomass).

The term lignocellulosic biomass" includes virtually any plant-derived organic matter (woody or non-woody) available for energy on a sustainable basis "Plant-derived" necessarily includes both sexually reproductive plant parts involved in the production of seed (e.g., flower buds, flowers, fruit, nuts, and seeds) and vegetative parts (e.g., leaves, roots, leaf buds and stems), Plant biomass can include, but is not limited to, agricultural crop wastes and residues such as corn stover, wheat straw, rice straw, sugar cane bagasse and the like. Plant biomass further includes, but is not limited to, woody energy crops, wood wastes and residues such as trees, softwood forest thinnings, barky wastes, sawdust, paper and pulp industry waste streams, wood fiber, herbal plant material brewing wastes, and the like. Additionally grass crops, such as switchgrass and the like have the potential to be produced in large-scale amounts and to provide a significant source of another plant biomass. For urban areas, potential plant biomass feedstock comprises yard waste (e.g., grass clippings, leaves, tree clippings, brush, etc.) and vegetable processing waste.

The peroxidase enzyme may be contacted with the lignocellulosic biomass whereby the enzyme has undergone at least one step of purification and is not provided together with the yeast cells which have been genetically modified to express the enzyme. Alternatively, yeast cells which are genetically modified to express the peroxidase enzyme are contacted with the lignocellulosic biomass. Still alternatively, the lignocellulosic biomass is contacted with fermentation medium into which the peroxidase enzyme has been secreted.

The present invention contemplates contacting the lignocellulosic biomass with at least one, at least two or even three of the peroxidase enzymes described herein (particular combinations provided herein above). Furthermore, additional enzymes may be used to further break-down the lignocellulosic biomass. Such enzymes include, but are not limited to cellulases, hemicellulases and xylanases.

The term "cellulase" when used generally can refer to enzymes involved in cellulose degradation. Cellulase enzymes are classified on the basis of their mode of action. There are two basic kinds of cellulases: the endocellulases, which cleave polysaccharide polymer chains internally; and the exocellulases, which cleave from the reducing and non-reducing ends of molecules generated by the action of endocellulases. Cellulases include cellobiohydrolases, endoglucanases, and β-D-glucosidases. Endoglucanases randomly attack the amorphous regions of cellulose substrates, yielding mainly higher oligomers. Cellulobiohydrolases are exocellulases which hydrolyze crystalline cellulose and release cellobiose (glucose dimer). Both types of enzymes hydrolyze-1,4-glycosidic bonds. β-D-glucosidases or cellulobiase converts oligosaccharides and cellubiose to glucose.

As used herein, the term "cellulase" is typically used more specifically to refer to the enzyme is cellulase (E.C. 3.2.1.4), also known as an endoglucanase, which catalyzes the hydrolysis of 1,4-β-D-glycosidic linkages. The cellulase can be of microbial origin, such as derivable from a strain of a filamentous fungus (e.g., *Aspergillus, Trichoderma, Humnicola, Fusarimm*). Commercially available cellulase preparations which can be used include, but are not limited to, CELLUCLAST™, CELLUZYME™, CEREFLO™, and ULTRAFLO™ (available from Novozymes AIS, Bagsvaerd, Denmark), SPEZYME™ CE and SPEZYME™ CP (available from Genencor International, Inc., Rochester, N.Y., United States of America) and ROHAMENT® CL (available from AB Enzymes GmbH, Darmstadt, Germany).

Hemicellulases are enzymes that are involved in hemicellulose degradation. Hemicellulases include xylanases, arabinofuranosidases, acetyl xylan esterases, glucuronidases, mannanases, galactanases, and arabinases. Similar to cellulase enzymes, hemicellulases are classified on the basis of their mode of action: the endo-acting hemicellulases attack internal bonds within the polysaccharide chain; the exo-acting hemicellulases act progressively from either the reducing or non-reducing end of polysaccharide chains. More particularly, endo-acting hemicellulases include, but are not limited to, endoarabinanase, endoarabinogalactanase, endoglucanase, endomannanase, endoxylanase, and feraxan endoxylanase. Examples of exo-acting hemicellulases include, but are not limited to, α-L-arabinosidase, β-L-arabinosidase, α-1,2-L-fucosidase, α-D-galactosidase, β-D-galactosidase, β-D-glucosidase, β-D-glucuronidase, β-D-mannosidase, β-D-xylosidase, exo-glucosidase, exo-cellobiohydrolase, exo-mannobiohydrolase, exo-mannanase, exo-xylanase, xylan α-glucuronidase, and coniferin β-glucosidase.

Depolymerization of lignin can result in the production of useful products including, but not limited to vanillin, syringaldehyde and ferulic acid. The present method may therefore further include a step of isolating the reaction products, as known in the art.

Production of second generation biofuel especially from lignocelluloses has received considerable attention in recent years due to its large scale availability and high energy content. The presence of lignin in the plant cell walls negatively impacts the conversion of biomass to biofuel. The conversion of biomass to biofuel is accomplished by fermentation of sugars preceded by pre-treatment and hydrolysis. Pre-treatment of biomass is required for delignification and hence effective fermentation of cellulose. Versatile peroxidases seem to be attractive solution for pre-treatment of biofuels as they efficiently deconstruct the lignocellulosic polymers without the requirement of redox mediators. The high redox potential of this class of heme peroxidases and ability to act independent of redox mediators are of great significance in their utilization for biofuel production.

Accordingly, the versatile peroxidases disclosed herein can be part of a process for producing a biofuel from lignocellulosic biomass.

The term "biofuel" refers to a fuel that is derived from biomass, i.e., a living or recently living biological organism, such as a plant or an animal waste.

Biofuels include, but are not limited to, biodisel, biohydrogen, biogas, biomass-derived dimethylfuran (DMF), and the like. In particular, the term "biofuel" can be used to refer to biomass-derived alcohols (e.g., bioalcohol), such as ethanol, methanol, propanol, or butanol, which can be denatured, if desired prior to use. The term "biofuel" can also be used to refer to fuel mixtures comprising biomass-derived fuels, such as alcohol/gasoline mixtures (i.e., gasohols). Gasohols can comprise any desired percentage of biomass-derived alcohol (i.e., about 10%, 15%, 20%, 25%, 30%. 35%, 40%. 45%, 50%, 55%, 60%, 65%, 70%, 75%, 80%, 85%, 90%, or 95% biomass-derived alcohol). For example, one useful biofuel-based mixture is E85, which comprises 85% ethanol and 15% gasoline.

Thus, following or concomitant with contacting the biomass with the peroxidase enzyme, the present inventors contemplate contacting the biomass with an enzyme composition (e.g. cellulose, xylanase and/or hemicellulose, as described herein above) to provide a fermentable sugar mixture; and fermenting the fermentable sugar mixture to provide an alcohol.

The terms "fermentable sugar" and "sugar" can be used interchangeably and refer to oligosaccharides, monosaccharides and mixtures thereof that can be used as a carbon source in a fermentation process. Fermentable monosaccharides include arabinose, glyceraldehyde, dihydroxyacetone, erythrose, ribose, ribulose, xylose, glucose, galactose, mannose, fucose, fructose, sedoheptulose, neuraminic acid, or mixtures of these. Fermentable disaccharides include sucrose, lactose, maltose, gentiobiose, or mixtures thereof. "Sugar" can also be used to refer to polysaccharides that require further enzymatic treatment prior to fermentation.

As mentioned, the peroxidase enzymes described herein show a very promiscuous activity and accordingly have a very wide range of applications, examples of which include:
(i) bio-remediation;
(ii) pulp bleaching;
(iii) animal feed production;
(iv) biofuel production;
(v) dye bleaching;
(vi) laundering; or
(vii) skin or hair lightening.

As used herein the term "about" refers to +10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Methods

VP sequence collection. VP sequences were extracted from three databases: MycoCosm (fungal genome database, RedoxiBase (oxidoreductases database), and fPoxDB (fungal peroxidases database). Signal peptide sequences were identified using SignalP-5.0 and were removed from the relevant sequences. A multiple sequence alignment was generated using MUSCLE based on all unique sequences, and a phylogenetic tree was inferred using the Maximum Likelihood method and JTT matrix-based model through MEGA. For each clade, a consensus sequence was generated using EMBOSS Cons, and the VP sequence with the highest similarity to the consensus was chosen for further analysis.

trRosetta structure modeling. The structures of all the selected sequences were calculated using the trRosetta structure prediction algorithm (December 2020 version). The models were visually inspected, and ones exhibiting poor parameters were eliminated; for instance, models that did not adopt the expected fold of VPs or in which the catalytic site diverged from expectation. Finally, twelve diverse sequences (eleven sequences from the analysis above and VPL), with 51-81% identity between each sequence pair, were selected for further modeling and design (see Tables 1 and 2, herein below).

Computational design calculations. For each sequence, the best-calculated model was subjected to design by a proprietary algorithm. VPL was also designed by the algorithm starting from its crystal structure (PDB code: 3FJW).

AlphaFold2 modelling. The sequences of 5H, 8H and 11H were structurally modeled by the AlphaFold2 algorithm.

Cloning of VP genes. Cloning of all VP genes was performed by using the S. cerevisiae homologous recombination machinery. pJRoC30-AAO (aryl-alcohol oxidase) expression shuttle vector was digested with BamHI and XhoI restriction enzymes to remove the signal peptide and the AAO gene constructed within it. The α-factor preproleader DNA sequence, that was used in a previous directed evolution campaign of VPL (including additional restriction site in its 3' that encodes for Glu-Phe dipeptide in the N-terminal of the mature proteins), was ordered as a gene fragment with 40 bp overlap to the linearized plasmid, and the VP genes were ordered each with 40 bp overlap to the signal peptide sequence, and to the linearized plasmid. The design of the 40 bp overlapping regions between the three fragments (plasmid, signal peptide, VP genes) allowed the recombination machinery of the protease-deficient S. cerevisiae strain BJ5465 to drive the fusion of the three DNA elements after transformation, and to form the pJRoC30-SignalPeptide-VPgene expression shuttle vector. pJRoC30-VPL-WT, -R4, and -2-1B were previously constructed. All S. cerevisiae-transformed cells were plated in synthetic complete (SC) drop-out plates, and in each plate, selected colonies were picked and sequenced to verify the correct assembly and gene sequence.

Culture media. Minimal medium is composed of 6.7 g/L yeast nitrogen base, 1.92 g/L amino acids supplements (yeast synthetic drop-out medium supplements without uracil), 2% raffinose and 25 mg/L chloramphenicol. VPs expression medium is composed of YP×1.11 medium (22.2 g bacto peptone and 11.1 g yeast extract), 67 mM $KH_2PO_4$ buffer at pH 6.0, 25 g/L ethanol, 22.2 g/L D-galactose, 500 mg/L bovine hemoglobin, 1 mM $CaCl_2$) and 25 mg/L chloramphenicol. SC drop-out plates are composed of 6.7 g/L yeast nitrogen base, 1.92 g/L amino acids supplements (yeast synthetic drop-out medium supplements without uracil), 2% glucose, 20 g/L Bacto agar and 25 mg/L chloramphenicol.

Screening for active variants. A colony from each S. cerevisiae clone containing the parental or mutant VP gene was picked from an SC drop-out plate, inoculated in 2 mL minimal medium in a culture tube, and incubated for 48 hours at 30° C. and 225 rpm. An aliquot of cells was removed and used to inoculate 2 mL of minimal medium in a new culture tube to an OD600 nm of 0.25-0.30, under the same conditions. The cells completed two growth phases (8-10 hours, reaching OD600 nm~ 1), then the expression medium (2.7 mL) was inoculated with 0.3 mL of the pre-culture in a new culture tube (OD600 nm~ 0.1). Cells were incubated for further ~38-40 hours at 30° C. and 225 rpm and then centrifuged at 4,000 g for 20 min at 4° C. The supernatant was removed into new tubes for further analysis. The expression protocol ran in triplicate, with an empty vector (containing only the signal peptide sequence) and the VPL-R4 and -2-1B variants as negative and positive controls, respectively. An ABTS-based colorimetric assay was conducted to assess the variants' activity: 20 μL of supernatant were transferred into activity 96 plates (Greiner Bio-One GmbH, Kremsmünster, Austria), and then, 180 μL of the reaction mixture were added to each row in the plate, and absorption at 418 nm was recorded immediately in a kinetic mode in a plate-reader at 25° C. (Citation5 or Synergy HTX plate readers, Bio-Tek, Bad Friedrichshall, Germany). The reaction mixture contained 100 4 mM citrate-phosphate buffer (pH 4.0), 2 mM ABTS and 0.1 mM $H_2O_2$. The activities were recorded in triplicate.

pH stability. Supernatants of the selected variants were diluted to reach a final concentration of 100 mM citrate-phosphate-borate buffer at pH ranging from 2-9. Aliquots of 20 μL were removed at different times (time 0, 4, 25, 50, 75, 165 hours) and measured in the regular ABTS-based colorimetric assay described above, but here in the presence of 180 μL of the following reaction mixture: 111.11 mM citrate-phosphate-borate buffer (pH 4.0), 2.22 mM ABTS and 0.111 mM $H_2O_2$. For pH 2, an additional experiment was conducted, under the same procedure but with aliquots being removed at different time points (time 0, 10, 20, 30, 45, 60, 75, 90, 120, and 150 min). For pH 2-9 range assay, activities were normalized to the activity at time 0 in pH=3, for residual activity calculations. All incubations and activity assays were conducted in triplicate.

Kinetic thermostability ($t_{1/2}$). Aliquots of 30 μL of selected variants' supernatant at appropriate dilutions (with 20 mM piperazine pH=5.5, buffer A, to achieve linear response in kinetic mode measurements in activity reads) were used for each incubation time point. The samples were incubated in a thermocycler (S1000™ thermocycler, Bio-Rad, Rishon LeZion, Israel) pre-heated to 60° C. or 65° C., and removed at different times (after 0, 2, 5, 7, 10, 15, 20, 30, 45, 60, 90 and 120 min), chilled on ice for 10 min and further incubated at room temperature at least for 10 min. Activity at each time point was measured using the ABTS-based colorimetric assay described above and was normalized to the activity at time 0 for residual activity calculations. All incubations and activity assays were conducted in triplicate.

Thermostability assay ($T_{50}$). Aliquots of 30 μL of selected variants' supernatant at appropriate dilutions (with buffer A, to achieve linear response in kinetic mode measurements in activity reads) were used for each incubation temperature. The samples were incubated for 10 or 15 minutes in a thermocycler pre-heated to a specific temperature (every 5° C. in a gradient scale ranging from 25 to 80° C.) and then removed and chilled on ice for 10 min. Thereafter, samples were removed from ice and incubated for at least 5 min at room temperature. Activity at each temperature was measured using the ABTS-based colorimetric assay described above and was normalized to the activity at 25° C. for residual activity calculations. All incubations and activity assays were conducted in triplicate. T50 values were calculated by sigmoidal fit to the T50 data of 5H, 8H, 11H and R4 (15 minutes incubation).

VPs production and purification. A colony from *S. cerevisiae* clone containing the VP gene (5H, 8H, 11H, VPL_R4, VPL_2-1B) was picked from an SC drop-out plate, inoculated in 25 mL minimal medium in a 250 flask, and incubated for 48 hours at 30° C. and 225 rpm. An aliquot of cells was removed and used to inoculate 100 mL of minimal medium in a 1 L flask to an $OD_{600\ nm}$ of 0.25-0.30, under the same conditions. The cells completed two growth phases (8-10 hours, reaching $OD_{600\ nm}$~1-1.5), then the expression medium (450 mL) was inoculated with 50 mL of the pre-culture in a 2 L flask ($OD_{600\ nm}$~0.1). Cells were incubated for a further ~60 hours at 30° C. and 225 rpm. Thereafter, cells were centrifuged at 6000 g for 15 min at 4° C., and the supernatant was collected and filtered with a 0.2 μm filter bottle.

Filtrates were subjected to fractional precipitation with ammonium sulfate in two steps: first cut of 50%, followed by centrifugation and elimination of the precipitates, and the second cut of 70%. Buffer A was used to dissolve the pellet, and the dissolved protein solution was shaken overnight at 4° C. for maximal recovery. The dissolved fraction was then centrifuged, filtrated, concentrated, and subjected to overnight dialysis against buffer A. Filtered fractions of the VP proteins after dialysis were uploaded into a HiTrap™ Q HP Column (GE Healthcare Bio-Sciences AB, Uppsala, Sweden) pre-equilibrated with buffer A, through ÄKTA pure protein purification system (GE Healthcare Bio-Sciences AB). Proteins were eluted in a two-step linear gradient from 0 to 1 M NaCl, at a flow rate of 1 ml/min: the first phase of 0-25% over 15 column volumes (75 min) and second phase of 25-100% over 2 column volumes (10 min). The fractions of the peak with the highest VP activity (and absorption at 407 nm) were pooled, concentrated, and dialyzed against 20 mM piperazine buffer pH=5.5 and 150 mM NaCl (buffer B). Protein fractions were then uploaded onto a Superdex 75 Increase 10/300 GL (GE Healthcare Bio-Sciences AB) through the ÄKTA pure system pre-equilibrated with buffer B. The fractions of the peak with the highest VP activity (and absorption at 407 nm) were pooled and dialyzed against buffer A. Pure protein samples were stored at 4° C. Protein concentration was determined using the BCA assay with bovine serum albumin as a standard. The obtained Reinheitszahl values (Rz: $Abs_{407\ nm}/Abs_{280\ nm}$), which indicate for the purity of peroxidases, were 1 for 8H (due to high tryptophan content) and above 2 for 5H, 11H, R4 and 2-1B.

Hydrogen peroxide stability. Purified 5H, 8H, 11H and R4 at 250 nM concentration (diluted with buffer A, to achieve linear response in kinetic mode measurements in activity reads) were incubated for 50 minutes at room temperature with 750 μM $H_2O_2$ (1:3,000 ratio). An aliquot of 20 μL was removed at times 0, 3, 7, 12, 18, 28, 38 and 48 minutes. Activity was immediately measured using the ABTS-based colorimetric assay described above and was normalized to the activity at time zero for residual activity calculations. All incubations and activity assays were conducted in triplicate.

pH activity profiles. For purified 5H, 8H, 11H, and R4, 20 μL protein samples (diluted in buffer A) were transferred into activity 96 plates (in the case of VA and $MnSO_4$, UV-Star plates; Greiner Bio-One GmbH, Kremsmünster, Austria) and then, 180 μL of the reaction mixture were added to each row in the plate, and absorption at the appropriate wavelength (substrate-dependent) was recorded immediately in a kinetic mode in a plate-reader at 25° C. The reaction mixtures contained a specific substrate in 100 mM citrate-phosphate-borate buffer (pH 2, 3, 3.5, 4, 5, 6, 7, 8) and 0.1 mM $H_2O_2$. The activities were recorded in triplicate. The following substrate concentrations and absorption wavelengths were used: ABTS: 2 mM, 418 nm; DMP: 5 mM, 469 nm; RB5: 0.05 mM, 598 nm; VA: 30 mM, 310 nm. For manganese, the reaction mixtures contained 60 mM $MnSO_4$ in 100 mM sodium tartrate buffer (pH 3, 3.5, 4, 4.5, 5) and 0.1 mM $H_2O_2$, and the $Mn^{3+}$-tartrate complex absorption was read at 238 nm. For each protein and substrate, the activities were normalized to the activity at optimal pH for residual activity calculations. Each activity assay was conducted in triplicate.

Kinetic parameters. Steady-state kinetics were determined for 5H, 8H, 11H and R4, by measuring the activity (initial rates) in increasing concentrations of the substrate, and the $K_M$ and $K_{cat}$ values were calculated by fitting the results to the Michaelis-Menten model ($V_0=K_{cat}ES/(K_M+S)$). 20 μL purified protein samples (diluted in buffer A to appropriate concentration) were transferred into activity 96 plates (in the case of VA and $MnSO_4$, UV-Star plates) and then, 180 μL of the reaction mixture were added to each row in the plate, and absorption at the appropriate wavelength (substrate-dependent) was recorded immediately in a kinetic mode in a plate-reader at 25° C. The reaction mixtures contained substrates at varying concentrations, in 100 mM citrate-phosphate-borate buffer at optimum pH (for manganese, sodium tartrate buffer was used) and optimum $H_2O_2$ concentration (0.4 mM for 5H, 0.2 mM for 8H, 0.1 mM for 11H and 1 mM for R4; approximately double of the $K_M$ values were used to gain high activity with minimal inhibition effect). $H_2O_2$ kinetics was measured using 2 mM (5H, 11H and R4) or 3 mM (8H) ABTS in 100 mM citrate-phosphate-borate buffer at optimum pH for ABTS activity. The following molar extinction coefficients were used to calculate the substrate/product concentration: ABTS, ε418 nm=36,000 $M^{-1}$ $cm^{-1}$; DMP, ε469 nm=27,500 $M^{-1}$ $cm^{-1}$; RB5, ε598 nm=30,000 $M^{-1}$ $cm^{-1}$; VA, ε310 nm=9300 $M^{-1}$ $cm^{-1}$; $Mn^{3+}$-tartrate, ε238 nm=6500 $M^{-1}$ $cm^{-1}$. All activities were recorded in triplicate and the average velocity was used for the kinetic constants calculations.

Expression level calculations. Enzyme concentrations, [E], were extracted from the Michaelis-Menten equation ($V_0=k_{cat}[S][E]/(K_M+[S])$) using the experimentally observed initial rates ($V_0$) (means of biological triplicates), ABTS concentration ([S]), and the kinetic constants calculated for ABTS ($K_M$ and $k_{cat}$) as reported in Table 4, herein below. The activity assay was performed at pH=4.0, and the initial activities were normalized to the activity at optimal pH (using the data from pH-dependent activity assay; FIG. 8).

Example 1: Computational Design for Functional Expression Directly from Sequence VP sequences were extracted from different databases, phylogenetically classified, and eleven sequences that exhibited 51-81% identity to one another were selected for modeling using trRosetta (FIGS. 1A, 1B; Tables 1 and 2).

TABLE 1

Selected VPs origins, protein lengths and number of mutations in each design

| Name | Species | Protein length | # mut. H | # mut. M | # mut. L |
|---|---|---|---|---|---|
| VP8 | *Ganoderma* sp. 10597_SS1 | 346 | 38 | 25 | 12 |
| VP2 | *Dichomitus squalens* | 353 | 29 | 18 | 11 |
| VP7 | *Trametes versicolor* | 338 | 49 | 22 | 13 |
| VP4 | *Lentinus tigrinus* ALCF2SS1-6s | 345 | 40 | 21 | 8 |
| VP3 | *Gelatoporia subvermispora* B | 338 | 38 | 21 | 15 |
| VP10 | *Pleurotus* sp. Florida | 344 | 33 | 22 | 11 |
| VPL | *Pleurotus eryngii* (VPL2) | 331 | 39 | 23 | 16 |
| VP5 | *Pleurotus ostreatus* | 339 | 43 | 27 | 18 |
| VP11 | *Pleurotus ostreatus* | 338 | 38 | 23 | 13 |
| VP9 | *Ganoderma* sp. 10597 SS1 | 335 | 30 | 19 | 11 |
| VP1 | *Bjerkandera adusta* | 340 | 27 | 14 | 7 |
| VP6 | *Physisporinus* sp. PF18 | 337 | 25 | 15 | 8 | mut refers the number of mutations in each designed variant:
H - high mutational load,
M - medium mutational load,
L - low mutational load.

TABLE 2

Selected VP sequences homology (in percentage)

| Name | VP8 | VP2 | VP7 | VP4 | VP3 | VP10 | VPL | VP5 | VP11 | VP9 | VP1 | VP6 |
|---|---|---|---|---|---|---|---|---|---|---|---|---|
| VP8 | 100 | 77 | 76 | 75 | 52 | 57 | 57 | 52 | 55 | 53 | 57 | 55 |
| VP2 |  | 100 | 80 | 81 | 51 | 58 | 58 | 53 | 58 | 52 | 57 | 55 |
| VP7 |  |  | 100 | 81 | 53 | 60 | 60 | 55 | 60 | 54 | 60 | 57 |
| VP4 |  |  |  | 100 | 83 | 59 | 59 | 54 | 58 | 55 | 59 | 56 |
| VP3 |  |  |  |  | 100 | 64 | 66 | 63 | 66 | 66 | 69 | 69 |
| VP10 |  |  |  |  |  | 100 | 73 | 66 | 76 | 68 | 68 | 72 |
| VPL |  |  |  |  |  |  | 100 | 69 | 78 | 68 | 70 | 71 |
| VP5 |  |  |  |  |  |  |  | 100 | 80 | 61 | 61 | 64 |
| VP11 |  |  |  |  |  |  |  |  | 100 | 66 | 68 | 72 |
| VP9 |  |  |  |  |  |  |  |  |  | 100 | 71 | 74 |
| VP1 |  |  |  |  |  |  |  |  |  |  | 100 | 76 |
| VP6 |  |  |  |  |  |  |  |  |  |  |  | 100 |

The top model in each case was then subjected to stability design using a proprietary algorithm (FIG. 1C; Goldenzweig 2016, ibid; Weinstein, 2020, ibid). VPL was also designed using the same algorithm based on its crystallographic structure (PDB entry: 3FJW). Notably, the new structure prediction methods do not model ligands and ions. The models were visually compared to the VPL experimental structure. It was found that the models retained the intricate arrangement of amino acids in the heme binding pocket and the ion-binding sites (FIGS. 5A-C). This observation led the present inventors to the realization that the trRosetta models could be used as reliable starting points for the design of enzymes as complex as the VPs. Based on the VPL crystallographic structure, the positions in each model which comprised the catalytic and ion-ligand sites was determined and the design at these positions was disabled. Design was also restricted in positions where model uncertainty was high and in adjacent positions. Finally, the wild type sequence was selected and three computational designs with different mutational loads (approximately 10 in the most conservative design and up to 43 mutations in the most permissive one; VPs are approximately 340 amino acids long i.e. roughly 12% of the protein template was mutated in the most permissive designs) was used for experimental characterization. The DNA encoding each protein was codon optimized for expression, ordered as synthetic gene fragments that were incorporated in the pJRoC30 plasmid downstream of the *S. cerevisiae* a factor prepro-leader, and transformed into yeast cells.

The approach described above yielded four functionally expressed VPs (FIG. 1D): VPL (from *Pleurotus eryngii*), two paralogs from *Pleurotus ostreatus* (VP5 and VP11; SEQ ID NOs: 2 and 3, respectively) and a VP from *Ganoderma* sp. 10597_SS1 (VP8; SEQ ID NO: 3; Table 3). For these VPs, the wild type progenitors demonstrated poor functional expression while the designs efficiently oxidized the peroxidase substrate 2,2'-azino-bis (3-ethylbenzothiazoline-6-sulfonic acid) (ABTS; FIG. 1D). Particularly, for all four VPs the most active design exhibits the highest mutational load (38-43 mutations, >10% of the sequence); the designs are therefore denoted as 5H (SEQ ID NO: 1), 8H (SEQ ID NO: 2), 11H (SEQ ID NO: 3), and VPLH (SEQ ID NO: 7) to designate their high mutational load. The designed mutations exhibit improved core packing, introduce new hydrogen-bond networks and rigidify loops (FIGS. 5A-C). Some of these mutations are radical (for example, Ile→Phe mutation in the core of the protein; FIG. 5A) and some are additive (creating hydrogen-bond networks; FIGS. 5B-5C), implying that successful incorporation of these mutations required highly accurate atomic model.

TABLE 3

| Active VP designs sequences homology (in percentage) | | | | |
|---|---|---|---|---|
| Name | VPL | 5H (SEQ ID NO: 1) | 8H (SEQ ID NO: 2) | 11H (SEQ ID NO: 3) |
| VPL | 100 | 74 | 66 | 81 |
| 5H | | 100 | 60 | 83 |
| 8H | | | 100 | 64 |
| 11H | | | | 100 |

In these four cases, the most active design exhibits the highest mutational load (38-43 mutations, >10% of the sequence); the designs are therefore denoted as 5H, 8H, 11H, and VPLH to designate their high mutational load. Since the wild type progenitors of the three VPs showed negligible functional expression, all further biochemical characterization was compared to the VPL variants R4 and 2-1B (previously evolved for expression and thermostability, respectively).

Example 2. Designed VPs are Highly Stable

Each of the designed VPs exhibited a unique stability profile. Although VPLH also demonstrated significantly enhanced functional expression compared to its wild type protein (FIG. 1D), it did not show substantial improvement relative to R4 and 2-1B (which are also derived from VPL) and was not pursued further.

The designed VPs exhibit higher thermal stability compared to R4 (FIGS. 2A, 2B and 6A-C). While the temperature at which the enzyme loses half of its maximal activity levels after 15 min incubation (T50) is similar to R4 across all designs (FIGS. 6A-C), at elevated temperatures, 5H does not lose its activity completely (FIG. 6A). In short incubation periods, 5H shows much enhanced activity at 45-60° C. compared to the activity at room temperature, similar to 2-1B, and the highest residual activity at 65-80° C. (FIG. 6B). This trend is consistent with the observed kinetic stability at 60-65° C. ($t_{1/2}$, the time at which the protein loses half of its activity after incubation at a specific temperature; FIG. 2B and FIG. 6C): 5H maintains stable residual activity even after two hours, comparable to 2-1B, which was evolved specifically to withstand high temperatures. Long-term heat resistance is an important advantage in industrial processes.

In nature lignin is decomposed under acidic conditions, and VP activity is strongly acid-dependent. Therefore, high oxidizing power depends on stability and activity at pH 2-3. 8H is stable under acidic to neutral pHs and is the most active VP after incubation in highly acidic pH (pH=2; FIGS. 2A and 7A-B). VPs may also be useful in alkaline conditions, for instance for biomedical purposes and for paper and textile processing. Remarkably, designs 5H and 11H maintain their initial activity levels even after one-week incubation at pH 9 (FIGS. 2A and 7A).

Hydrogen peroxide is the terminal electron acceptor in VPs but at high concentrations it also causes protein deactivation. To assess the stability at high hydrogen peroxide concentrations, VPs were incubated with $H_2O_2$ at 1:3,000 molar ratio (FIG. 2C). Further, the $H_2O_2$ affinities were assessed (see Table 4). In the case of 11H, there is no correlation between the apparent KM and the t½. While R4, 5H and 8H $H_2O_2$ affinities are 12-, 5- and 2-fold lower than seen in 11H, respectively.

Lastly, the expression levels of all VPs was estimated based on initial rate measurements of the yeast broth and the kinetic constant data (Table 4). Under these circumstances, the three VP designs show much greater functional-expression levels than R4, which is the highest functionally expressed VPL variant (FIG. 2A; Garcia-Ruiz, 2012, ibid). Further gains in functional expression can be made by optimizing the experimental conditions or expression strain.

Example 3. Designs Exhibit Diverse Functional Profiles

The activity profiles of the top-three VP designs were tested with a range of peroxidase substrates using R4 as a reference (FIGS. 3, 8 and Table 4).

TABLE 4

| Kinetic parameters with various substrates | | | | | |
|---|---|---|---|---|---|
| Substrate | Kinetic constants | 5H | 8H | 11H | R4 |
| ABTS (high efficiency) | $K_M$ (µM) | 1.9 ± 0.4 | 5.0 ± 0.8 | 6.3 ± 0.7 | 0.39 ± 0.08 |
| | $K_{cat}$ (sec$^{-1}$) | 1.5 ± 0.1 | 7.8 ± 0.3 | 2.0 ± 0.1 | 1.3 ± 0.1 |
| | $K_{cat}/K_M$ (sec$^{-1}$ mM$^{-1}$) | 763 ± 151 | 1550 ± 260 | 314 ± 37 | 3,300 ± 700 |
| ABTS (low efficiency) | $K_M$ (µM) | 765 ± 96 | 795 ± 96 | 1,100 ± 90 | 987 ± 107 |
| | $K_{cat}$ (sec$^{-1}$) | 33.2 ± 1.8 | 28.2 ± 0.9 | 11.2 ± 0.3 | 400 ± 21 |
| | $K_{cat}/K_M$ (sec$^{-1}$ mM$^{-1}$) | 43.4 ± 5.9 | 35.4 ± 4.4 | 10.3 ± 0.9 | 405 ± 49 |
| DMP (high efficiency) | $K_M$ (µM) | 85.7 ± 16.9 | 22.9 ± 1.8 | 168 ± 10 | 1.4 ± 0.3 |
| | $K_{cat}$ (sec$^{-1}$) | 1.2 ± 0.1 | 2.2 ± 0.1 | 1.91 ± 0.04 | 0.74 ± 0.05 |
| | $K_{cat}/K_M$ (sec$^{-1}$ mM$^{-1}$) | 14.4 ± 3.0 | 94.6 ± 8.2 | 11.4 ± 0.7 | 542 ± 113 |
| DMP (low efficiency) | $K_M$ (µM) | 27,700 ± 7,100 | 164 ± 12 | 11,400 ± 2,000 | 16,100 ± 1,700 |
| | $K_{cat}$ (sec$^{-1}$) | 5.4 ± 0.6 | 3.6 ± 0.1 | 6.3 ± 0.4 | 132 ± 7 |
| | $K_{cat}/K_M$ (sec$^{-1}$ mM$^{-1}$) | 0.19 ± 0.05 | 22.1 ± 1.6 | 0.55 ± 0.10 | 8.2 ± 1.0 |
| Mn$^{2+}$ | $K_M$ (µM) | 3,500 ± 200 | 11,300 ± 1,400 | 289 ± 34 | 523 ± 28 |
| | $K_{cat}$ (sec$^{-1}$) | 9.1 ± 0.1 | 0.64 ± 0.03 | 19.7 ± 0.5 | 78.3 ± 1.1 |
| | $K_{cat}/K_M$ (sec$^{-1}$ mM$^{-1}$) | 2.6 ± 0.1 | 0.06 ± 0.01 | 68.1 ± 8.2 | 150 ± 8 |
| VA | $K_M$ (µM) | 158 ± 27 | 10,100 ± 400 | 2,000 ± 100 | 7,400 ± 1,000 |
| | $K_{cat}$ (sec$^{-1}$) | 0.52 ± 0.02 | 5.5 ± 0.1 | 1.38 ± 0.03 | 5.4 ± 0.4 |
| | $K_{cat}/K_M$ (sec$^{-1}$ mM$^{-1}$) | 3.3 ± 0.6 | 0.55 ± 0.02 | 0.68 ± 0.05 | 0.7 ± 0.1 |

TABLE 4-continued

Kinetic parameters with various substrates

| Substrate | Kinetic constants | 5H | 8H | 11H | R4 |
|---|---|---|---|---|---|
| RB5 | $K_M$ (μM) | 2.9 ± 1.0 | 17.3 ± 1.7 | 2.0 ± 0.2 | 1.3 ± 0.1 |
| | $K_{cat}$ (sec$^{-1}$) | 0.18 ± 0.04 | 1.1 ± 0.1 | 0.30 ± 0.01 | 0.63 ± 0.02 |
| | $K_{cat}/K_M$ (sec$^{-1}$ mM$^{-1}$) | 62.3 ± 25.2 | 65.0 ± 7.2 | 152 ± 20 | 487 ± 51 |
| $H_2O_2$ | $K_M$ (μM) | 197 ± 20 | 89.7 ± 12.9 | 38.9 ± 6.9 | 457 ± 53 |
| | $K_{cat}$ (sec$^{-1}$) | 20.3 ± 0.8 | 12.1 ± 0.6 | 7.0 ± 0.5 | 230 ± 9 |
| | $K_{cat}/K_M$ (sec$^{-1}$ mM$^{-1}$) | 103 ± 11 | 135 ± 21 | 180 ± 35 | 503 ± 61 |

VPs exhibit a very broad substrate scope, and accordingly, five substrates that represent different redox potentials and chemical structures were selected: ABTS and 2,6-dimethoxyphenol (DMP; low-redox potential substrates), veratryl alcohol (VA; a high-redox potential substrate), reactive black 5 (RB5; a high-redox potential dye) and $Mn^{2+}$. DMP, VA, and $Mn^{2+}$ are likely to be native substrates of white-rot VPs, since VPs functionalize them for oxidizing lignin. VA and RB5 are exclusively oxidized by the high-redox potential surface-active tryptophan, while DMP and ABTS are oxidized both in the heme pocket (low-) or by the tryptophan (high-efficiency site). Furthermore, $Mn^{2+}$ is oxidized in a distinct active site. Thus, the five substrates probe the reactivity and selectivity of each of the three VP active sites. Remarkably, despite the structural complexity, the lack of co-factors in the model structures, the very large number of mutations in each design, the designs retained activity towards all of the substrates. These results indicate that the combination of ab initio modeling and computational design is effective even in complex, multifunctional enzymes.

Furthermore, the four VPs show the expected preference for acidic conditions (FIGS. 3 and 8). Nevertheless, pH preferences vary dramatically among the designs. For instance, 8H exhibits a strong preference for low pH (2-3) in DMP and VA oxidation, whereas 5H is non-reactive at low pH and is reactive at relatively high pH where 8H is inactive. Furthermore, whereas R4 exhibits relatively broad pH reactivity for DMP, it is more restricted in pH scope on the other substrates relative to the designs. Manganese oxidation as a function of pH shows unexpected trends. Typically, VPs exhibit a pH optimum of 5 for oxidizing $Mn^{2+}$ (as in R4; Garcia-Ruiz, 20212, ibid). 8H also exhibits a pH optimum of 5, despite the fact that this design exhibits a more acidic pH optimum for the other substrates. By contrast, 5H and 11H have a pH optimum at 4 and 4.5, respectively, closer to the native conditions in which white-rot fungi operate (pH approximately 3).

Next, the reactivity profiles of the three designs and R4 were tested relative to the substrates discussed above, again noting dramatic differences (FIG. 3 and Table 4). 8H and R4 are the most efficient enzymes in terms of their turnover numbers ($k_{cat}$), and R4 affinity to many substrates is the greatest, as reflected in low $K_M$. Substrate affinities, however, exhibit surprising diversity without establishing any of the enzymes as best across the board. First, although 5H exhibits low $k_{cat}$ values throughout, it exhibits more than an order of magnitude higher affinity for VA than the next best enzyme. Considering that VA has the highest redox potential of all substrates and is a non-phenolic component of lignin, the enzyme's high affinity for VA may be valuable for complete decomposition of lignin at low VA concentrations. Second, as described above, 11H exhibits the highest affinity to $H_2O_2$ (by an order of magnitude relative to R4). Since $H_2O_2$ deactivates VPs, high affinity in this enzyme is beneficial in cases where hydrogen peroxide levels must be kept low to maintain activity in other enzymes. 11H is also the most $H_2O_2$-stable variant, making it an attractive enzyme for use in different $H_2O_2$ concentrations. Third, the heme-dependent affinity of 8H is at least 70-fold higher for DMP relative to the other VPs. Last, 11H exhibits the highest affinity for manganese, by at least twofold (relative to R4).

Figure 4A:
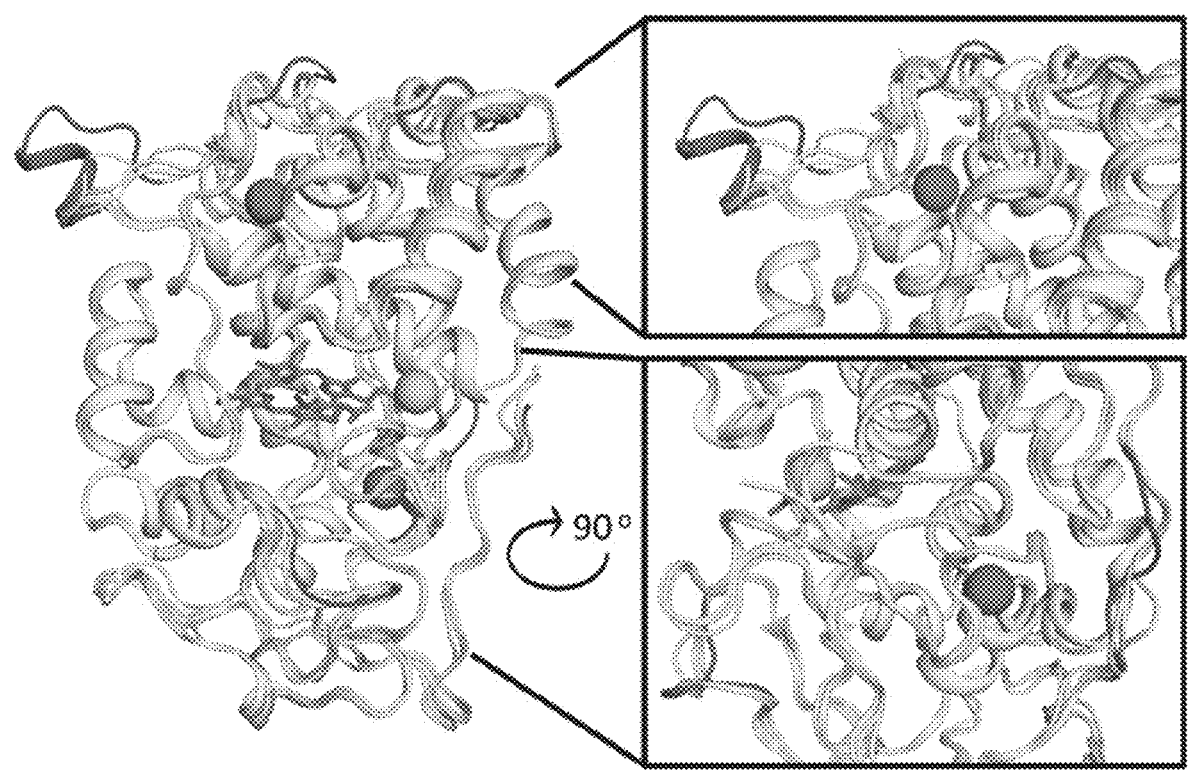
Figure 4B:
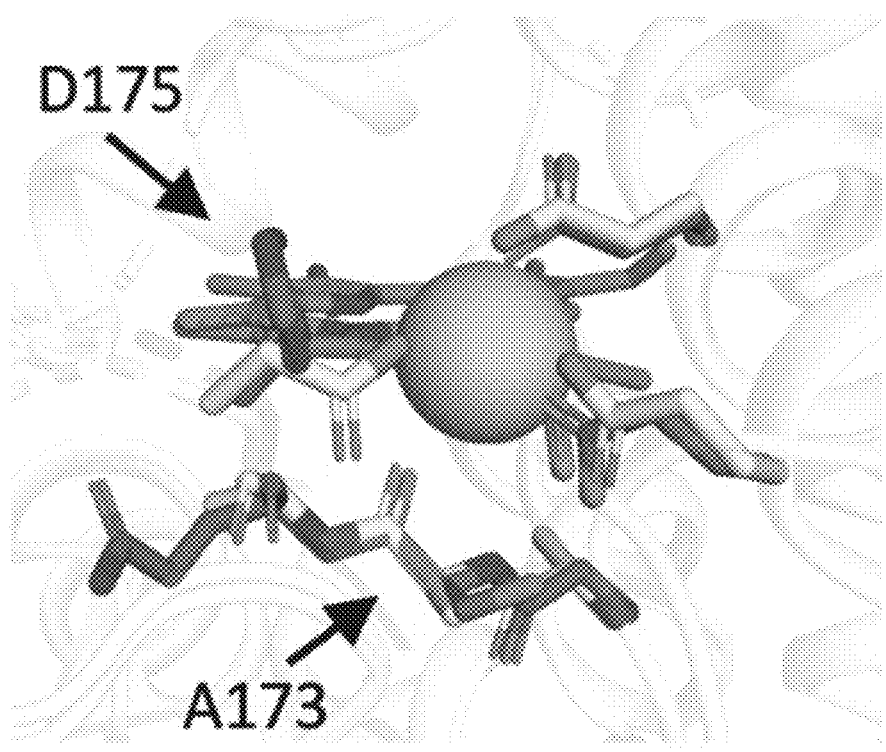

Example 4. The Structural Basis for Functional Diversity in Designed VPs 8H was designed based on a VP from the Polyporales order, whereas the other designs, as well as R4, derive from the Agaricales order (and specifically, from genus *Pleurotus*). Thus, 8H diverges from the other VPs both in sequence (Tables 2 & 3) and in structure (FIG. 4A). The most significant active-site differences between 8H and the other VPs are in a loop that chelates both heme and manganese (FIG. 4B). Among the manganese-chelating residues, 8H exhibits an Asp→His mutation in position 175 (all position numbers relative to PDB entry 3FJW), which was previously implicated in manganese oxidation. Additionally, mutation Ala173Ser near the manganese binding site may also modify manganese-binding properties. These naturally occurring sequence changes likely explain the sharp decrease in manganese oxidation ability in 8H.

Figure 4C:
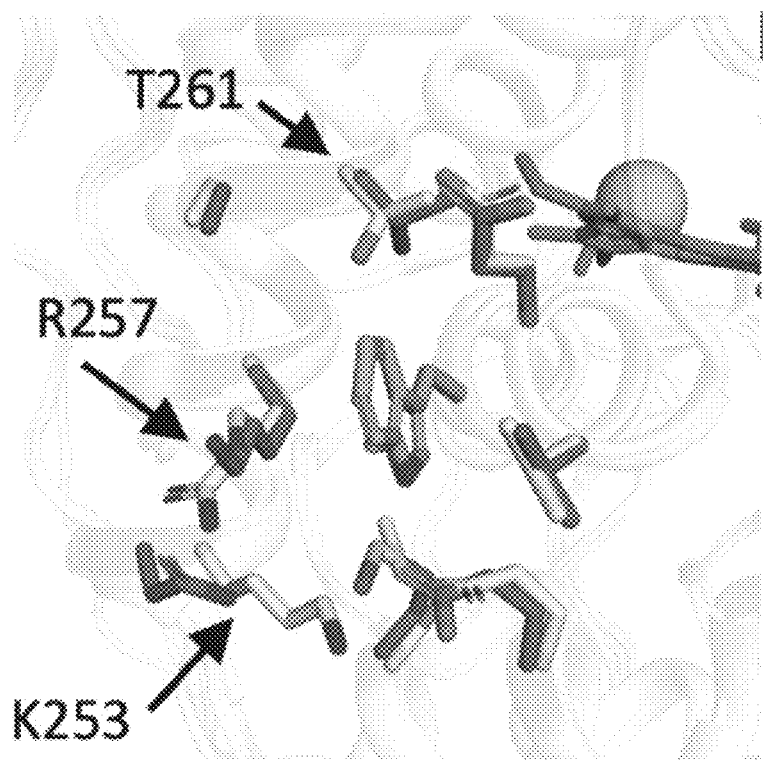

In addition to the manganese oxidation site, VPs oxidize substrates through a high-redox surface tryptophan site via a long-range electron-transfer mechanism, and a low-redox potential heme-dependent site. The four VPs that were investigated exhibit large variations in kinetic constants in the high-redox surface site. Thus, despite the high accessibility of this site, the tryptophan environment's chemical properties and molecular recognition plays an important role in determining reactivity at this site. 8H shows unique electrostatic and structural properties at this site as well: whereas the other enzymes exhibit a conserved Lys and Arg that partially shield the tryptophan and a Thr residue on the opposite side, 8H has an Asn, Lys and Val, respectively (FIG. 4C). Although 5H, 11H and R4 share an identical sequence at the high-redox potential tryptophan active site, they exhibit significant changes in reactivity. These reactivity differences may stem from sequence changes along the electron-relay path that connects the tryptophan radical and the heme-dependent site in ways that remain to be clarified.

Figure 4D:
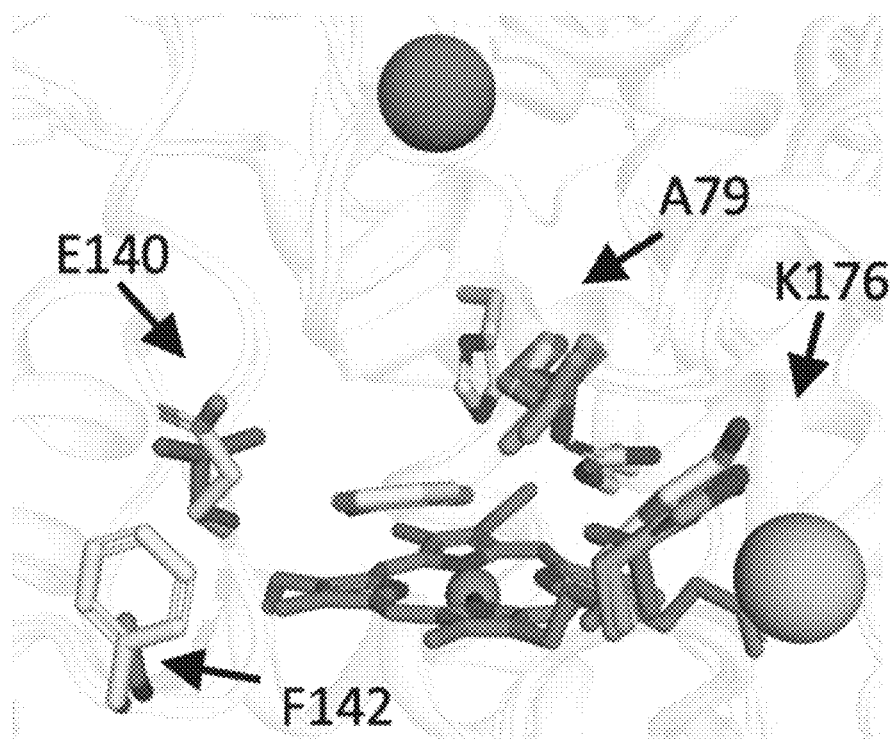

Finally, the models show that the heme pocket is conserved among all the VPs. The only variations in its immediate surroundings are the manganese-bridging loop in 8H, a Ser→Ala substitution in position 168 in 5H and hydrophobic-to-hydrophobic substitutions at positions 152, 234 and 262 in all VPs. Given these minor sequence changes, we speculate that the ABTS and DMP activity differences stem from changes in substrate accessibility to the home-binding pocket. Indeed, in heme access-channel loops, dramatic variations exist in several positions which influence the hydrophobicity of the pocket and its size. For example, 8H has a Leu instead of Glu in position 140, generating a hydrophobic access channel that may underlie the observed higher affinity for DMP; this mutation in 8H may also lead to higher affinity for the product, explaining the low turnover number (FIG. 4D). Previous mutation analyses demonstrated this position's importance for substrate recognition and pH-dependent activity. It can be concluded that the significant diversity observed among natural VPs underlies the large functional changes observed among the present designs.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A peroxidase enzyme comprising:
   (i) an amino acid sequence at least 85% identical to SEQ ID NO: 2; and
   (ii) mutations set forth in R4P, M5S, E34T, G59A, T65W, A67Q, V85I, V95I, P104H, I107Q, T125V, S135P, S141P, D143P, S161Q, S164A, S167A, D172S, D229Q, A247L, S249A, S252P, R265Q, A266D, L269Q, A270S, E273A, G274A, A288S, T290I, A299P, T300P, S323D, A325P, S330P, A333P, A335P and A341P, wherein coordinates of said mutations correspond to said SEQ ID NO: 2;
   wherein the peroxidase enzyme is characterized by increased yield when expressed in yeast cells as compared to wild-type peroxidase enzyme having an amino acid sequence as set forth in SEQ ID NO: 5.

2. The peroxidase of claim 1, being at least 95% identical to SEQ ID NO: 2.

3. The peroxidase enzyme of claim 1 having a Km or a Kcat for a substrate selected from the group consisting of 2,2′-azino-bis(3-ethylbenzothiazoline-6-sulfonic acid (ABTS), 2,6-dimethoxyphenol (DMP), veratryl alcohol (VA), reactive black 5 (RB5) and $Mn^{2+}$ as set forth in Table 4 or FIG. 3;
having a pH stability profile according to FIG. 7A.

4. A polynucleotide comprising a nucleic acid sequence encoding the peroxidase enzyme of claim 1.

5. A yeast cell comprising the enzyme of claim 1, optionally the yeast cell is a *Saccharomyces cerevisiae* cell.

6. A method of producing a peroxidase enzyme, the method comprising expressing in yeast the polynucleotide of claim 4, thereby producing the peroxidase enzyme.

7. The method of claim 6, further comprising isolating the peroxidase enzyme from the yeast or conditioned medium thereof.

8. A culture comprising a biomass composition which comprises lignin and a population of yeast cells expressing at least one peroxidase enzyme of claim 1.

9. The culture of claim 8, wherein the culture is a silage.

10. The culture of claim 8, further comprising yeast cells which express a peroxidase enzyme having an amino acid sequence at least 85% identical to SEQ ID NO: 7.

11. A method of degrading lignin comprising contacting the lignin with at least one peroxidase enzyme of claim 1 or with a cell which expresses the at least one peroxidase enzyme under conditions that allow the peroxidase enzyme to depolymerize the lignin, thereby degrading the lignin.

12. The method of claim 11, wherein the lignin is comprised in lignocellulosic plant material.

13. The method of claim 11, further comprising contacting the lignin with at least one additional enzyme selected from the group consisting of a cellulose and a xylanase.

14. The method of claim 11, further comprising isolating at least one reaction product following the degrading.

15. The method of claim 14, wherein said reaction product is a biofuel.

16. The method of claim 14, wherein said reaction product is selected from the group consisting of vanillin, syringaldehyde and ferulic acid.

17. The peroxidase of claim 1, being at least 99% identical to SEQ ID NO: 2.

18. The peroxidase of claim 1, being identical to SEQ ID NO: 2.

* * * * *

```
                          SEQUENCE LISTING

Sequence total quantity: 8
SEQ ID NO: 1              moltype = AA  length = 339
FEATURE                   Location/Qualifiers
source                    1..339
                          mol_type = protein
                          note = versatile peroxidases variants
                          organism = synthetic construct
SEQUENCE: 1
VSLPQKRATC SGGQTTSNEA CCVLFDLMED LQKNLFDGGQ CGEQAHEALR LTFHDAIGFS    60
PSRGVMGGAD GSVITFSDIE TNFPANLGID DIVEAEKSFL QRHNISAGDL VHFAATLAVT   120
NCPGAPRIPF FLGRPPATAP SPPGLVPEPF DSVTDILARM ADAGFSPVEV VWLLSAHSVA   180
AADHVDPTIP GTPFDSTPNL FDSQFFIETQ LRGTTFPGTG GNPGEVKSPL PGEMRLQSDH   240
LFARDPRTAC EWQSMVNDQQ KIQDRFRDTL FKMSMLGQNQ DDMIDCSDVI PVPPPLTTKP   300
HLPAGKSKTD VEQACATAPF PTLPADPGPP TSVPPVPPA                          339

SEQ ID NO: 2              moltype = AA  length = 346
FEATURE                   Location/Qualifiers
source                    1..346
                          mol_type = protein
                          note = versatile peroxidases variants
                          organism = synthetic construct
SEQUENCE: 2
AVPPSGKRAT CSNGKTVNND ACCVWFDVLD DIQTNLFHGG QCGEDAHEAL RLTFHDAIAF    60
SPALWAQGQF GGGGADGSII AHSDIELTYP ANNGIDEIVE ASRHIAQKHN VSFGDFIQFA   120
GAVGVANCNG GPQLPFFAGR PNPSQPAPPN LVPLPSDSAD QILARFADAG FSAVEVVWLL   180
VSHTVGSQHT VDPSIPGAPF DSTPSDFDAQ FFVETMLNGT LVPGNGLQQG EVNSPYPGEF   240
RLQSDFLLAR DPRTACEWQK MIADQDNMQS KFAAVMLKMS LLGFDQSSLI DCSDVIPTPP   300
GTVQDPFLPA GLTVDDLQPA CSDSPFPTVP TVPGPATSIP PVPMDS                  346

SEQ ID NO: 3              moltype = AA  length = 338
FEATURE                   Location/Qualifiers
source                    1..338
                          mol_type = protein
                          note = versatile peroxidases variants
                          organism = synthetic construct
SEQUENCE: 3
VTLPQKRATC SGGQTTSNAA CCVLFDLRDD LQKNLFDGGQ CGEEVHESLR LTFHDAIGFS    60
PTKGGGADG SVLIFSDTEL NFPANLGIDE IVEAQKPFLQ RHNISAGDLV QFAGALGVSN   120
CPGAPRIPFF LGRPPATAPS PDGLVPEPFD SVDDILARMA DAGFSPVEVV WLLSSHTIAA   180
ADHVDPTIPG TPFDSTPSIF DSQFFIETQL RGTLFPGTGG NPGEVESPLP GEIRLQSDHL   240
LARDPRTACE WQSMVDNMPK IQNRFAATML KMSLLGQNVR DLIDCSDVIP TPPPLVGTAH   300
LPAGKTQSDV EQACATTPFP TIPADPGPVT SVPPVPPS                           338

SEQ ID NO: 4              moltype = AA  length = 339
FEATURE                   Location/Qualifiers
source                    1..339
                          mol_type = protein
                          organism = Pleurotus ostreatus
SEQUENCE: 4
VSLPQKRATC AGGQVTANAA CCVLFPLMED LQKNLFDDGA CGEDAHEALR LTFHDAIGFS    60
PSRGVMGGAD GSVITFSDTE VNFPANLGID EIVEAEKPFL ARHNISAGDL VHFAGTLAVT   120
NCPGAPRIPF FLGRPPAKAA SPIGLVPEPF DTITDILARM DDAGFVSVEV VWLLSAHSVA   180
AADHVDETIP GTPFDSTPNL FDSQIFIETQ LRGISFPGTG GNHGEVQSPL KGEMRLQSDH   240
LFARDDRTSC EWQSMTNDQQ KIQDRFSDTL FKMSMLGQNQ DAMIDCSDVI PVPAALVTKP   300
HLPAGKSKTD VEQACATGAF PALGADPGPV TSVPRVPPA                          339
```

```
SEQ ID NO: 5            moltype = AA  length = 346
FEATURE                 Location/Qualifiers
source                  1..346
                        mol_type = protein
                        organism = Ganoderma sp.
SEQUENCE: 5
AVPRMGKRAT CSNGKTVNND ACCVWFDVLD DIQENLFHGG QCGEDAHEAL RLTFHDAIGF   60
SPALTAAGQF GGGGADGSII AHSDVELTYP ANNGVDEIVE ASRPIAIKHN VSFGDFIQFA  120
GAVGTANCNG GPQLSFFAGR SNDSQPAPPN LVPLPSDSAD SILSRFSDAG FDAVEVVWLL  180
VSHTVGSQHT VDPSIPGAPF DSTPSDFDAQ FFVETMLNGT LVPGNGLQDG EVNSPYPGEF  240
RLQSDFALSR DSRTACEWQK MIADRANMLA KFEGVMLKMS LLGFDQSALT DCSDVIPTAT  300
GTVQDPFLPA GLTVDDLQPA CSSSAFPTVS TVAGAATSIP AVPMDS                346

SEQ ID NO: 6            moltype = AA  length = 338
FEATURE                 Location/Qualifiers
source                  1..338
                        mol_type = protein
                        organism = Pleurotus ostreatus
SEQUENCE: 6
VTLPQKRATC AGGQVTANAA CCVLFPILED LQQNLFDGGE CGEEVHESLR LTFHDAIGFS   60
PTKGGGGADG SVLTFSDPEV NFPANLGIDE IVEAQKPFLA RHNISAGDLV QFAGALGVSN  120
CPGAPRIPFF LGRPPAKAAS PIGLVPEPFD TVTDILDRMG DAGFAAVEVV WLLSSHTIAA  180
ADHVDESIPG TPFDSTPSIF DSQFFIETQL RGTSFPGSGG NHGEVESPLA GEIRLQSDHL  240
LARDSRTSCE WQSMVDNMPK IQNRFAATML KMSLLGQNQA DLIDCSDVIP TPPALVGKAH  300
LPAGKVQSDV EQACATTPFP AIAADPGPVT AVPPVPPS                         338

SEQ ID NO: 7            moltype = AA  length = 331
FEATURE                 Location/Qualifiers
source                  1..331
                        mol_type = protein
                        note = versatile peroxidases variants
                        organism = synthetic construct
SEQUENCE: 7
ATCSDGRTTS NAACCVWFDI LDDIQTNLFD GGQCGEEVHE ALRLTFHDAI GFSPTLGGGG   60
ADGSIIIFDE IETNFPANAG IDEIVNAQKK FVQKHNISAG DFIQFAGAVG VSNCPGGVRI  120
PFFLGRPDAT APSPDGLVPE PFDSVDKILA RMADAGFSPV EVVWLLASHS IAAADKVDPT  180
IPGTPFDSTP GVFDSQFFIE TQLKGTLFPG TGGNKGEALS PLQGEIRLQS DFLLARDPRT  240
ACEWQSMVNN QEKIQSAFAA AMAKMALLGQ DKSKLVDCSD VIPTPPPLTG SAHLPAGFSL  300
NDVEQACSAT PFPTLSADPG PVTSVPPVPG S                                331

SEQ ID NO: 8            moltype = AA  length = 331
FEATURE                 Location/Qualifiers
source                  1..331
                        mol_type = protein
                        organism = Pleurotus eryngii
SEQUENCE: 8
ATCDDGRTTA NAACCILFPI LDDIQENLFD GAQCGEEVHE SLRLTFHDAI GFSPTLGGGG   60
ADGSIIAFDT IETNFPANAG IDEIVSAQKP FVAKHNISAG DFIQFAGAVG VSNCPGGVRI  120
PFFLGRPDAV AASPDHLVPE PFDSVDSILA RMGDAGFSPV EVVWLLASHS IAAADKVDPS  180
IPGTPFDSTP GVFDSQFFIE TQLKGRLFPG TADNKGEAQS PLQGEIRLQS DHLLARDPQT  240
ACEWQSMVNN QPKIQNRFAA TMSKMALLGQ DKTKLIDCSD VIPTPPALVG AAHLPAGFSL  300
SDVEQACAAT PFPALTADPG PVTSVPPVPG S                                331
```